Figure 1:
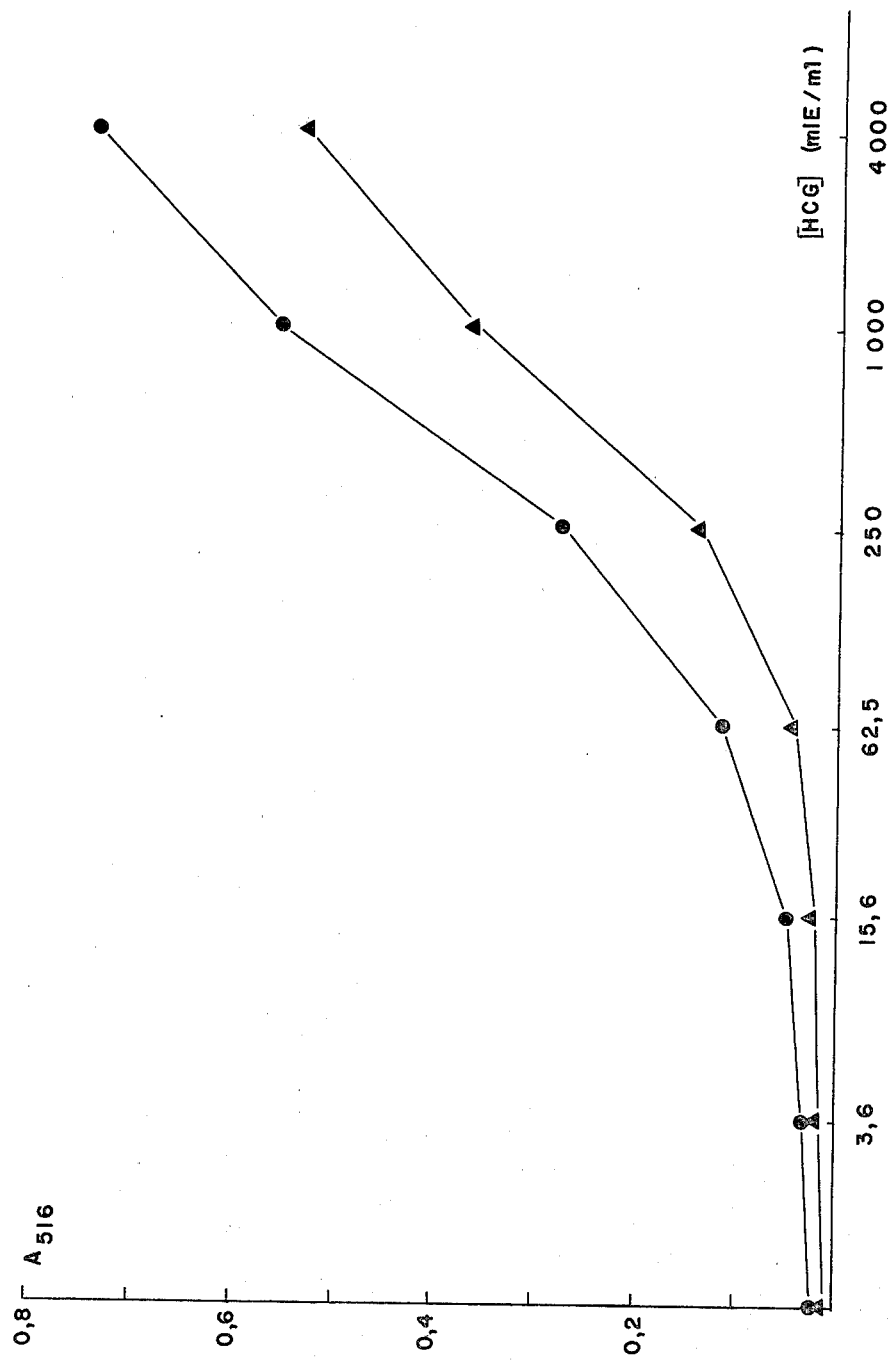

United States Patent [19]

Gribnau et al.

[11] 4,373,932

[45] Feb. 15, 1983

[54] APPLICATION OF WATER-DISPERSIBLE HYDROPHOBIC DYES OR PIGMENTS AS LABELS IN IMMUNOASSAYS

[75] Inventors: Thomas C. J. Gribnau, Haren; Frits Roeles, Dreumel; Johannes H. W. Leuvering, Heesch, all of Netherlands

[73] Assignee: Akzona Incorporated, Asheville, N.C.

[21] Appl. No.: 222,263

[22] Filed: Jan. 2, 1981

[30] Foreign Application Priority Data

Jan. 11, 1980 [NL] Netherlands .......................... 8000173

[51] Int. Cl.$^3$ ................... G01N 33/54; G01N 33/58; G01N 33/76; G01N 33/74

[52] U.S. Cl. ........................................ 436/501; 8/526; 8/527; 422/61; 435/7; 436/531; 436/805; 436/538

[58] Field of Search ................ 23/230 B, 915; 424/12, 424/3, 7, 8; 8/526, 527; 422/61; 252/408

[56] References Cited

U.S. PATENT DOCUMENTS

| Number | Date | Name | Class |
|---|---|---|---|
| 3,449,488 | 6/1969 | Bozicevich | 424/8 |
| 3,641,235 | 2/1972 | Weiss | 424/8 |
| 3,720,760 | 3/1973 | Bennich et al. | 424/1 |
| 3,853,987 | 12/1974 | Dreyer | 424/1 |
| 3,900,558 | 9/1975 | Kinsolving | 424/8 |
| 3,939,350 | 2/1976 | Kronick et al. | 250/365 |
| 3,941,876 | 3/1976 | Marinkovick | 424/1 |
| 3,992,631 | 11/1976 | Harte | 250/365 |
| 3,996,345 | 12/1976 | Ullman et al. | 424/12 |
| 3,998,943 | 12/1976 | Ullman | 424/12 |
| 3,999,948 | 12/1976 | Deindorfer et al. | 23/230 B |
| 4,001,400 | 1/1977 | Hager | 424/134 |
| 4,011,219 | 3/1977 | Nishii et al. | 260/250 P |
| 4,025,310 | 5/1977 | Bolz et al. | 23/230 B |
| 4,036,946 | 7/1977 | Kleinerman | 424/8 |
| 4,058,732 | 11/1977 | Wieder | 250/461 B |
| 4,104,029 | 8/1978 | Maier, Jr. | 23/230 B |
| 4,108,972 | 8/1978 | Dreyer | 424/1 |
| 4,160,016 | 7/1979 | Ullman | 424/8 |
| 4,160,018 | 7/1979 | Bjorklund | 424/12 |
| 4,160,019 | 7/1979 | Bjorklund | 424/12 |
| 4,160,818 | 7/1979 | Smith et al. | 424/8 |
| 4,161,515 | 7/1979 | Ullman | 424/8 |
| 4,163,779 | 8/1979 | Harte et al. | 424/1 |
| 4,168,146 | 9/1979 | Grubb et al. | 23/230 B |
| 4,169,137 | 9/1979 | Hirschfeld et al. | 424/8 |
| 4,181,650 | 1/1980 | Maier, Jr. | 260/112.7 |
| 4,187,075 | 2/1980 | Noller | 23/230 B |
| 4,197,361 | 4/1980 | Hoff et al. | 424/8 |
| 4,199,599 | 4/1980 | Ullman et al. | 424/8 |
| 4,200,436 | 4/1980 | Mochida et al. | 23/230 B |
| 4,201,763 | 5/1980 | Monthony et al. | 424/8 |
| 4,207,075 | 6/1980 | Leburdy | 23/230 B |
| 3,985,867 | 10/1976 | Redshaw | 424/12 |
| 4,166,105 | 8/1979 | Hirshfeld | 23/230 BX |
| 4,278,653 | 7/1981 | Harris | 23/915 X |
| 4,254,219 | 3/1981 | Fullerton | 435/7 |
| 4,194,877 | 3/1980 | Peterson | 8/526 |
| 4,202,815 | 5/1980 | Wegmann | 8/526 X |
| 4,286,959 | 9/1981 | Horn | 8/527 X |
| 4,302,536 | 11/1981 | Longenecker | 424/8 X |
| 4,020,151 | 4/1977 | Bolz | 424/1.5 |
| 4,115,535 | 9/1978 | Giaever | 424/1 |
| 4,152,412 | 5/1979 | Brewer | 424/7 |
| 4,177,253 | 12/1979 | Davies | 424/1 |
| 4,223,002 | 9/1980 | Newman | 424/1 |
| 4,225,485 | 9/1980 | Buckler | 260/112 B |
| 4,261,968 | 4/1981 | Ullman | 424/8 |
| 4,006,360 | 2/1977 | Mueller | 250/461 B |
| 4,331,444 | 5/1982 | Mihara I | 23/230 B |
| 4,337,063 | 6/1982 | Mihara II | 23/230 B |
| 4,323,647 | 4/1982 | Monjii et al. | 435/7 |
| 3,935,074 | 1/1976 | Rubenstein et al. | 195/103.5 R |
| 3,951,748 | 4/1976 | Devlin | 195/103.5 R |
| 3,992,516 | 11/1976 | Lim | 424/8 |
| 3,996,344 | 12/1976 | Gross | 424/1.5 |
| 3,997,657 | 12/1976 | Dziobkowski et al. | 424/3 |
| 4,011,308 | 3/1977 | Giaever | 424/1.5 |
| 4,016,250 | 4/1977 | Saxena | 424/1 |
| 4,018,884 | 4/1977 | Cleeland, Jr. et al. | 424/7 |
| 4,056,724 | 11/1977 | Harte | 250/328 |
| 4,061,466 | 12/1977 | Sjöholm et al. | 23/230 B |
| 4,067,959 | 1/1978 | Bolz | 424/1 |
| 4,069,352 | 1/1978 | Parson, Jr. | 424/7 |

(List continued on next page.)

FOREIGN PATENT DOCUMENTS

| Number | Date | Country |
|---|---|---|
| 15519 | 9/1980 | European Pat. Off. |
| 2557419 | 6/1976 | Fed. Rep. of Germany . |
| 79/00310 | 1/1980 | PCT Int'l Appl. |
| 79/00685 | 4/1980 | PCT Int'l Appl. |
| 79/00184 | 10/1980 | PCT Int'l Appl. |
| 81/01883 | 7/1981 | PCT Int'l Appl. |
| 1566423 | 4/1980 | United Kingdom . |

OTHER PUBLICATIONS

Hirschfeld, T., "Optical Microscopic Observation of Single Small Molecules," Applied Optics, vol. 15, No. 12, pp. 2965-2966 (Dec. 1976).

Hirschfeld, T., "Quantum Efficiency Independence of the Time Integrated Emission from a Fluorescent Molecule," Applied Optics, vol. 15, No. 12, pp. 3135-3139 (Dec. 1976).

(List continued on next page.)

*Primary Examiner*—Sidney Marantz
*Attorney, Agent, or Firm*—Robert H. Falk; Charles A. Wendel; Francis W. Young

[57] ABSTRACT

Processes, reagents and test kits for the qualitative and/or quantitative determination of an immunochemically reactive component, in which one or more labelled components are used, that are obtained by direct or indirect coupling of such a component or components to particles of an aqueous dispersion of a hydrophobic dye or pigment, or of polymer nuclei coated with such a dye or pigment.

During the reaction or after an adequate reaction time the nature and/or the quantity of the dye is determined in the test medium, or optionally after a separation of the bound and free labelled components in one of the fractions.

65 Claims, 7 Drawing Figures

U.S. PATENT DOCUMENTS

| | | | |
|---|---|---|---|
| 4,097,586 | 6/1978 | Gross | 424/1 |
| 4,098,876 | 7/1978 | Piasio et al. | 424/1 |
| 4,130,462 | 12/1978 | Rubenstein et al. | 195/103.5 A |
| 4,152,411 | 5/1979 | Schall | 424/1 |
| 4,153,675 | 5/1979 | Kleinerman | 424/8 |
| 4,174,384 | 11/1979 | Ullman et al. | 424/8 |
| 4,222,743 | 9/1980 | Wang | 23/230 B |
| 4,254,096 | 3/1981 | Monthony et al. | 424/8 |
| 4,256,834 | 3/1981 | Zuk et al. | 435/7 |
| 4,284,412 | 8/1981 | Hansen et al. | 23/230 B |
| 4,208,479 | 6/1980 | Zuk et al. | 435/7 |
| 4,211,766 | 7/1980 | Bjorklund | 424/88 |
| 4,215,102 | 7/1980 | Lee | 424/3 |
| 4,220,450 | 9/1980 | Maggio | 23/230 B |
| 4,222,744 | 9/1980 | McConnell | 23/230 B |
| 4,225,783 | 9/1980 | Palin et al. | 250/302 |
| 4,231,750 | 11/1980 | Dowben et al. | 23/230 B |
| 4,234,563 | 11/1980 | Rippe | 424/8 |
| 4,235,869 | 11/1980 | Schwarzberg | 424/8 |
| 4,238,195 | 12/1980 | Boguslaski et al. | 23/230 B |
| 4,238,395 | 12/1980 | Buckler et al. | 260/326 N |
| 4,248,854 | 2/1981 | Lukens, Jr. | 424/8 |
| 4,251,514 | 2/1981 | Rippe | 424/8 |
| 4,258,130 | 3/1981 | Ashton et al. | 435/7 |
| 4,248,965 | 2/1981 | Mochida et al. | 435/7 |
| 4,252,783 | 2/1981 | Kam et al. | 424/8 |
| 4,254,097 | 3/1981 | Rippe | 424/8 |
| 4,259,313 | 3/1981 | Frank et al. | 424/8 |
| 4,272,505 | 6/1981 | Smith | 424/8 |
| 4,272,506 | 6/1981 | Schwarzberg | 424/8 |
| 4,277,437 | 7/1981 | Maggio | 422/61 |
| 4,279,992 | 7/1981 | Boguslaski et al. | 435/7 |
| 4,283,382 | 8/1981 | Frank et al. | 424/8 |
| 4,294,817 | 10/1981 | Burgett et al. | 424/8 |
| 4,296,201 | 10/1981 | Ax et al. | 435/7 |
| 4,297,273 | 10/1981 | Buckler et al. | 260/112 B |
| 4,298,687 | 11/1981 | Maes | 435/7 |
| 4,302,534 | 11/1981 | Halmann et al. | 435/6 |
| 4,314,026 | 2/1982 | Descamps-Latscha | 435/7 |
| 4,318,707 | 3/1982 | Litman et al. | 23/230 B |
| 4,318,846 | 3/1982 | Khanna et al. | 260/112 B |
| 3,773,625 | 11/1973 | Sternberger et al. | 195/99 |
| 4,193,983 | 3/1980 | Ullman, et al. | 424/12 |
| 4,203,716 | 5/1980 | Chen | 430/207 |
| 3,789,116 | 1/1974 | Kay | 424/8 |

OTHER PUBLICATIONS

S. Fazekas et al., Biochimica et Biophysica Acta, 71, 377-391 (1963).

T. Gribnau, "Synthesis and Application of Immunosorbents Based on Halpyrimidine or Reactive Azo-dye Activated Polysaccharides—Influence of Ligand Modification on the Performance of Immunosorbents", Inst. Nat'l. Sante Rech. Med. (INSERM) (Les Collogues de l'Inserm, Affinity Chromatography) 86 at 175-186 (Jun. 1979).

T. C. Gribnau, et al., "Microscopic Observations on Commercial Sepharose, Deviations from Normal Bead Structure", Febs Letters (FEBLAL) 57(3) at 301-303 (1975).

Bauke K. Van Weemen, et al., "Coupling of Enzymes to Proteins and Haptens", (in Ligand Assay: Anal. Int. Dev. Isot. Nonisot. Immunoassay, pub.: Masson, New York, N.Y., 1981, Eds.: John Langan, Jeremy J. Clapp) at pp. 103-111.

T. C. Gribnau, et al., "Ligand Leakage in Affinity Chromatography, Mathematical Approach", Expermentia (EXPEAM) 30(10) at 1228-1230 (1974).

T. C. Gribnau, et al., "Application of the FCP-activation Procedure to the Synthesis of a Bio-Specific Adsorbent for Trpsin", J. Solid-Phase Biochem. (JSBIDL) 3(4) at 271-289 (1978).

T. C. Gribnau, et al., "Coupling of Effector Molecules to Solid Supports, Development of an Alternative to the Cyanogen Bromide Activation of Polysaccharides", J. Solid-Phase Biochem. (JSBIDL) 3(1) at 1-33 (1979, but Mtg. date 1978).

T. C. Gribnau, et al., "Alternatives to the Cyanogen Bromide Activation for Ligand Immobilization on Agarose", Lecture, Chem. Soc. Int. Symp., Chromatography of Synthetic Bio-Chemical Polymers 2 at 258-264 (1978, Pub.: Wiley, London, Roger Epton, Ed.).

T. C. Gribnau, et al., "Microscopic Observations on Agarose Beads, Dehydration by Solvent Exchange as an Alternative to Lyophilization", J. Chromatogr. (JOCRAM) 132(3) at 519-524 (1977).

Jan H. W. Leuvering, "A Sol Particle Agglutination Assay for Human Chorionic Gonadotrophin", J. Immunol. Methods (JIMMBG) 45(2) at 183-184 (1981).

T. C. J. Gribnau, Thesis, University of Nijmegen [Holland], 1977.

J. H. W. Leuvering, P. J. H. M. Thal, M. van der Woart, and A. H. W. M. Schuurs, "Sol Particle Immunoassay (SPIA)", J. Immunoassay 1(1) at 77-91 (1980).

J. H. W. Leuvering, P. J. H. M. Thal, M. van der Woart, and A. H. W. M. Schuurs, "Sol Particle Immunoassay for Human Chorionic Gonadotrophin, " Fres. Z. Anal. Chem. 301 at 132 (1980).

Mithal Hassan, et al., "Multi-Fluorescein-substituted polymers as Potential Labels in Fluoroimmunoassay: A System for Improved Detection Synsitivity", Febs Letters 103(2) at 339-341 (1979).

Maxim, P. E.; Veltri, R. W.; and P. M. Sprinkle: "Soluble Tumor Associated Markers in Lung Cancer Extracts", Oncology (Basel) (ONNCOB), 38(3) at 147-153 (1981).

Bergstrom, K. and Lefvert, A. K.: "An Automated Turbidimetric Immunoassay for Plasma Proteins, " Scand. J. Clin, Lab. Invest. (SJCLA) 40(7) at pp. 637-640 (1980).

Khanna, P. L., and Ullman, E. F.: "4'5'Di Methoxy-6-Carboxy Fluorescein a Novel Di Pole Di Pole Coupled Fluorescence Energy Transfer Acceptor Useful for Fluorescence Immunoassay, " Anal. Biochem. (ANBCA), 108(1), pp. 156-161 (1980).

Lin, T. M.; Halbert, S. P.; and O'Connor, G. R.: "Standardized Quantitative Enzyme Linked Immunoassay for Antibodies to Toxoplasma—Gondii", J. Clin. Microbiol. (JCMID) 11(6) pp. 675-681 (1980).

van der Werf, P. and Chang, C. H.: "Determination of Thyroxine Binding Globulin in Human Serum by Fluorescence Excitation Transfer Immunoassay", J. Immunol. Methods (JIMMB), 36(3-4), pp. 339-438 (1980).

Balsari, A.; Poli, G.; Molina, V.; Dovis, M.; Petruzzelli, E.; Boniolo, A.; and Rolleri, E.: "Enzyme Linked Immuno Sorbent Assay for Toxoplasma Antibody Detection: A Comparison with Other Sero Diagnostic Tests", J. Clin. Pathol. (Lond.) (JCPAA) 33(7), pp. 640-643 (1980).

Nicoli, D. F.; Briggs, J.; and Elings, V. B.: "Fluorescense Immunoassay Based on Long Time Correlations of Number Fluctuations", Proc. Natl. Acad. Sci., U.S.A. (PNASA), 77(8), pp. 4904-4908 (1980).

Ngo, T. T. and Lenhoff, H. M.: "A Sensitive and Versatile Chromogenic Assay for Peroxidase and Peroxidase-Coupled Reactions", Anal. Biochem. (ANBCA) 105(2) pp. 389-397 (1980).

Blaabjerg, O. and Petersen, P. H.: "Effect of Aggregates on Albumin Standardization", Scand. J. Clin. Lab. Invest. (SJCLA) 39(8) pp. 751-758 [1979].

Horobin, Richard W., and Flimming, Linda: "Structure-Staining Relationships in Histochemistry and Biological Staining, II, Mechanistic and Practical Aspects of the Staining of Elastic Fibers", J. Microsc. (Oxford) (JMICAR), 119(3) pp. 357-372 (1980).

Wood, Peter J.: "The Interaction of Direct Dyes with Water Soluble Substituted Delluloses and Cerial beta--glucans", Ind. Ens. Chem. Prod. Rex. Dev. (IEPRA6) 19(1), pp. 19-23, (1980).

Marshall, P. N.: "Commercially Available 'Pure' Azure Dyes—Caveat Emptor", Histochem. J. (HISJAE) 11(4) pp. 489-493 (1979).

Puchtler, Holde; Waldrop, Faye Sweat; and Meloan, Susan N.: "Effects of Acetylation and Benzoylation on Dye Binding: Investigation of Molecular Alterations in Models", Histochemistry (HCMYAL) 58(1-2), pp. 65-70 (1978).

Scholtz, C. L.: "Quantitative Histochemistry of Myelin Using Luxol Fast Blue MBS", Histochem. J. (HISJAE) 9(6), pp., 759-765 (1977).

Tiffe, H. W.; Matzke, K. H.; and Theissen, G.: "The Acridine Dyes: Their Purification, Physico Chemical, and Cytochemical Properties, II, Purification of Acriflavine and Proflavine and Their Cytochemical Behavior Regarding Machine-Oriented Evaluation", Histochemistry (HCMYAL) 53(1) pp. 63-77 (1977).

J. E. Scott, "The Molecular Biology of Histochemical Staining by Cationic Phthalocyanin Dyes: The Design of Replacements for Alcian Blue", J. MICROSC. (Oxford) (JMICAR), *119* (3) pp. 373-81 (1980).

R. Daoust, "The Histochemical Demonstration of Polycytidylic Acid and Polyuridylic Acid Hydrolases in Rat Liver Durins azo Dye Carcinosenesis", J. HISTOCHEM. CYTOCHEM. (JHCYAS) 25(6) pp. 458-65 (1977).

J. Tas, "Polyacrylamide Films as a Tool for Investigating Qualitative and Quantitative Aspects for the Staining of Glycosaminoglycans with Basic Dyes", HISTOCHEM. J. (HISJAE) 9(3) pp. 267-76 (1977).

Albert H. Coons, et al., "The Demonstration of Pneumococcal Antigen in Tissues by the Use of Fluorescent Antibody", J. IMMUNOLOGY *45*(2) at 159-170 (1942).

D. M. Weir, HANDBOOK OF EXPERIMENTAL IMMUNOLOGY (F. A. Davis Co., Philadelphia, Pa.; Blackwell Scientific Pub., London) at 423-462 and 571-596 (1967).

R. C. Nairn, "Immunological Tracing: General Considerations: Special Methods" (in FLUORESCENT PROTEIN TRACING, Ed. by R. C. Nairn, Williams & Wilkins, Baltimore) at 144-151 (1969).

Albert H. Coons, "Fluorescent Antibody Methods" (in GENERAL CYTOCHEMICAL METHODS, Volume 1, ed. by J. F. Danielli, Academic Press, Inc., New York) at pp. 400-422 (1958).

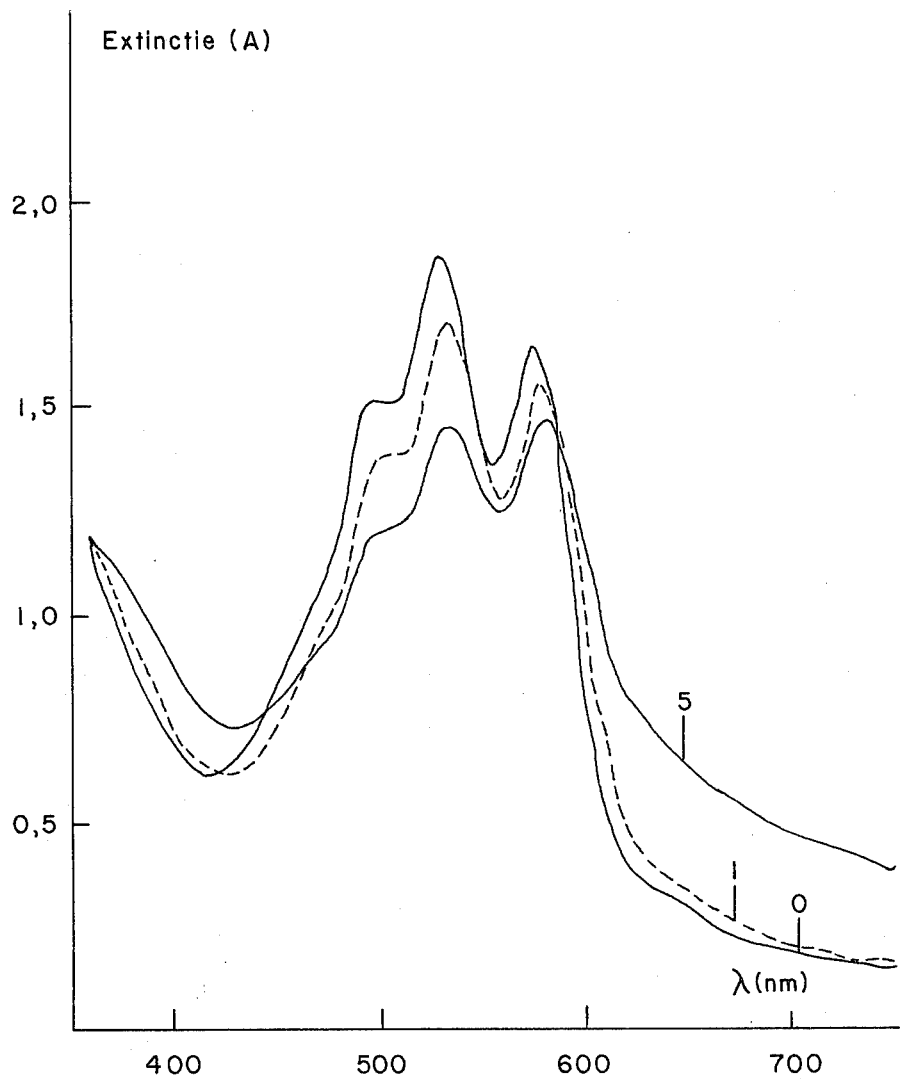
FIG. 3    Spectra of a Palanil<sup>R</sup> Red BF sol/rabbit anti-HCG immunoglobulin conjugate, in the presence of 0, 1, and 5 IU HCG/ml, respectively, after incubation during 20 h at room temperature (cf. p.9).

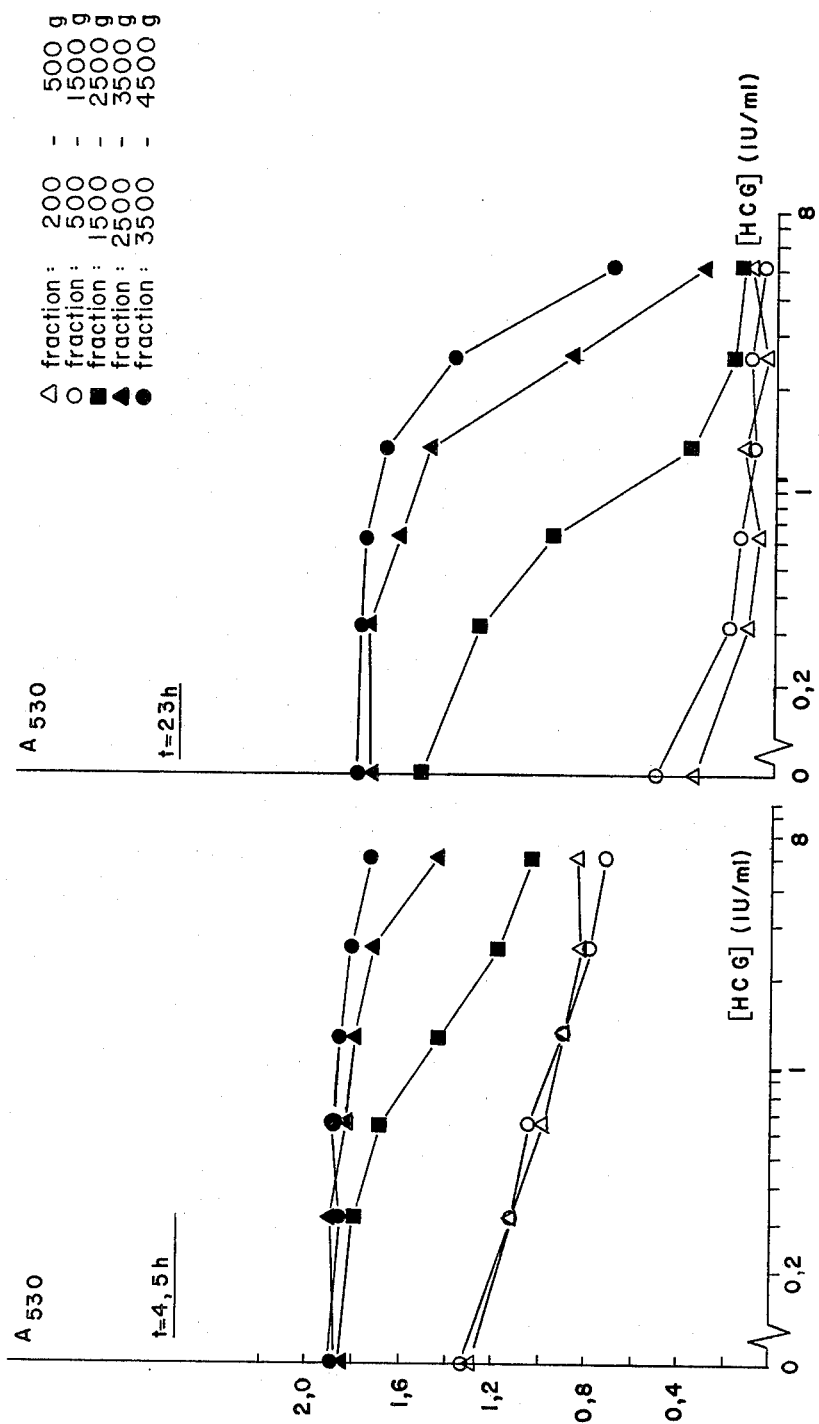

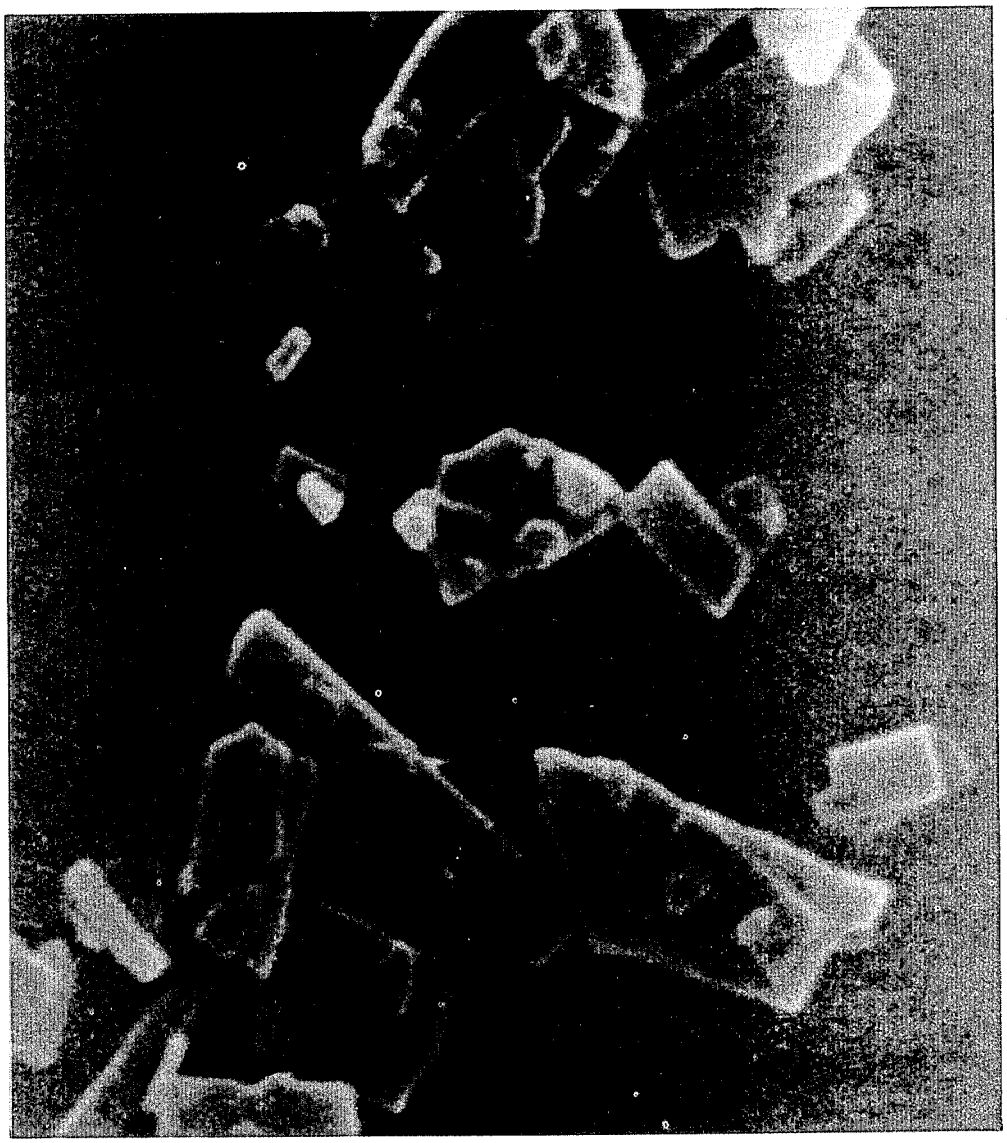
FIG. 5  Scanning electron microscope photo (enlargement: 15.000 X) of a sol of the transfer dye Lurafix Red BF prepared according to the method as described in Example 9.2.2.a.

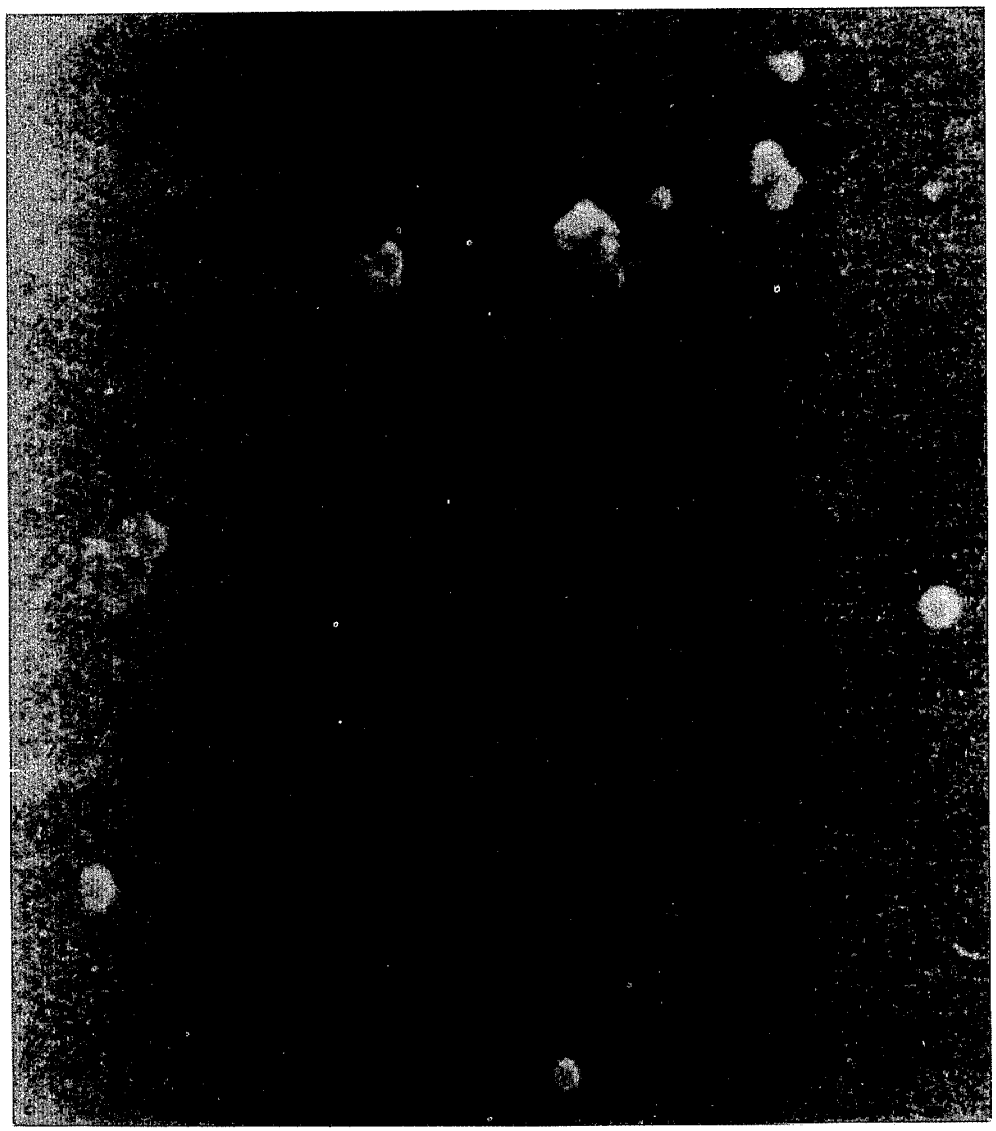
FIG. 6  Scanning electron microscope photo (enlargement: 15.000 X) of a sol of the transfer dye Lurafix Red BF prepared according to a method as described in Example 9.2.2.b.

APPLICATION OF WATER-DISPERSIBLE HYDROPHOBIC DYES OR PIGMENTS AS LABELS IN IMMUNOASSAYS

The present invention relates to a method for the qualitative and quantitative determination of an immunochemically reactive component such as a hapten, antigen or antibody in an aqueous test medium, employing the principle of the specific interaction between such immunochemically reactive components.

A large number of methods are known whereby substances can be determined in a qualitative and/or quantitative manner, based on the formation of specific immuno complexes. A variety of analytical techniques are available for the direct or indirect detection of the finally-formed immune complexes. Apart from reading off with the naked eye, physical methods are often widely used, such as spectrophotometry, fluorimetry, nephelometry and electron-dark field microscopy. These methods can be combined with the use of a label or tracer. Instead of detecting the actual immune complex, the label, coupled with one of the components of the complex, is then detected, so that a considerably lower detection limit can be attained.

As examples of qualitative immunochemical techniques we can mention the classical precipitin reaction (Heidelberger and Kendall, 1930) and immuno-diffusion—similarly based on immuno-precipitation—(Ouchterlony, 1948) followed in 1953 by immunoelectrophoresis developed by Grabar. In the latter-mentioned two methods antigen and antibody encounter each other via diffusion in an agar gel. The resultant precipitation line can, whether after prior coloring or not, be perceived by the naked eye. One disadvantage of these, as such simple methods is that diffusion takes a rather long time and that the detection limit is relatively high.

Quantitative methods of determination based on the principle of immuno-precipitation were developed by Mancini (1965; radial immuno-diffusion) and Laurell (1966; rocket-electrophoresis). Disadvantages of these methods are similarly a rather long determination period and/or a relatively high detection limit.

Apart from these non-labelled immunochemical techniques, in the course of years a number of labelled techniques have been developed, among which we can mention the haemagglutination test where one of the components is attached to the surface of erythrocytes; the technique of immunofluorescence where one of the components is labelled with a fluorescent compound (fluorophore), the radio-immunoassay developed by Yalow and Berson around 1959 whereby, instead of a fluorophore a radio-active atom or radio-active group is used as the tracer; and the most recent technique of enzyme immunoassay, on which the first publications appeared in 1971 from two groups working independently of each other, these being the Swedish investigators Engvall and Perlmann and the Dutchmen Schuurs and van Weemen. In principle the latter assay is analogous with the known radio-immunoassays with the distinction that instead of radioactive tracing, an enzyme is used as label.

Radio immunoassays which are widely used have undoubtedly shown great value, but they are afflicted by a number of significant shortcomings such as the risk factor because of working with radioactive materials, the high costs of reagents and equipment, the short stability of radioactively-labelled reagents, and the requirement that only qualified personnel may perform such assays.

The enzyme immunoassay does not suffer from these disadvantages, but nevertheless it is desirable that new assay techniques be developed which are even more sensitive, can be performed more rapidly, can be more easily automated, and/or enable the simultaneous determinaton of several immuno components.

The present invention relates to an immunoassay which, with respect to the final detection of the immunocomplex, is characterised by the application of, for one or more labelled immunochemically reactive components, obtained by direct or indirect coupling of such a component or components to particles of an aqueous dispersion of a hydrophobic dye or pigment, or of polymeric nuclei coated with such a dye or pigment, whereby during or after a certain reaction time for the immunochemical reaction, possibly after separation of the free and bound labelled component(s), the nature and/or the quantity of the dye is determined in the test medium, or in one of the fractions obtained after separation using known methods; the determination giving a qualitative or quantitative indication of the immunochemical reactive component(s) to be determined.

The "dispersed dye immunoassay" (DIA) developed in accordance with the present invention is considerably simpler than the "Radio Immunoassay" (RIA), because during the final detection use can be made of a simple reading by eye and/or of a simple colorimeter. As compared with the "Enzyme Immunoassay" (EIA, ELISA$^R$, EMIT$^R$) the determination is simpler and more rapid because the enzyme/substrate incubation can be omitted. Furthermore, it is possible to determine two or more components simultaneously by application of such chromophores as labels, that are clearly distinguishable spectrophotometrically. Finally the advantage of a dye as label which can be synthesized reproducibly, which can be characterised exactly by analytical/chemical methods and which is stable (in the form of a colloidal particle) is evident as compared with radioactive and enzyme labels of limited stability, and/or variable batch quality; on the other hand detection limits are at least equivalent. Sols of dispersed dyes have advantages over metal sols (e.g. gold), in colorimetric assays, due to the considerably higher molar absorbances of the dye sols as compared to the metal sols; for example:

gold sol (particle size 50 nm): 3300 l.mole$^{-1}$·cm$^{-1}$
disperse dyes (5.000–80.000 l.mole$^{-1}$·cm$^{-1}$; cf. K. Venhataraman: "The Analytical Chemistry of Synthetic Dyes", Wiley & Sons, 1977).

In addition, the color can be intensified (increase in absorbance) during the final determination of the dye label by dissolving the dye sol particles into an organic solvent (e.g. ethanol, methanol, iso-propanol). For example:

| label | $\lambda_{max}(nm)(sol)$ | $\lambda_{max}(nm)(EtOH)$ | $A\lambda_{max}^{1\ cm*}$ | $\epsilon^{**}$ |
| --- | --- | --- | --- | --- |
| Palanil ® Luminous Yellow G | 496 | | 70,77 | 28300 |
| Luminous Yellow G | | 464 | 110,36 | 44100 |
| Palanil ® Luminous Red G | 520 | | 48,33 | 19300 |

-continued

| label | $\lambda_{max(nm)(sol)}$ | $\lambda_{max(nm)(EtOH)}$ | $A\lambda_{max}^{1\ cm*}$ | $\epsilon^{**}$ |
|---|---|---|---|---|
| Red G | | 544 | 88,27 | 35300 |

*$1 \cdot g^{-1} \cdot cm^{-1}$
**$1 \cdot mole^{-1} \cdot cm^{-1}$

To the group of colored organic compounds which are applicable in the form of a hydrophobic sol in the invention described here, belong all the hydrophobic organic dyes and pigments which are insoluble in water or soluble only to a very limited extent.

Among these we should also include the water-soluble organic dyes, insofar as these in suitable concentrations form association colloids which, whether after prior cross-linking or not, can be stabilised. Furthermore it is also possible to use the leuco-vat dyes which are soluble in alkaline aqueous medium, and which can be converted by oxidation into their original colored and water-insoluble form; these also include the leuco-vat dyes which are water soluble and stabilised in the form of a sulphate half-ester. Another useful group is the group of dye components which, soluble as such in water and whether or not colored, after coupling to each other in situ, for example via oxidation or diazo coupling, can be converted into water-insoluble dyes. The following groups can be mentioned as examples of the above-mentioned dyes, using for this purpose the official color Index nomenclature: "disperse dyes, solvent dyes, pigments, vat dyes, sulphur dyes, mordant dyes, solubilised (leuco) vat dyes, solubilised (leuco) sulphur dyes, azoic dyes, oxidation bases, ingrain dyes" and "transfer dyes" which have not yet been officially named.

The colloidal dye particles to be applied as labels can be prepared by a large number of methods which are already known; see for example: Kruyt (Ed.) (1952) "Colloid Science", Vol. I, Elsevier, Amsterdam; Venkataraman (Ed.): "The Chemistry of Synthetic Dyes", Academic Press, New York, Vol. I (1952), II (1952), III (1970), IV (1971), V (1971); VI (1972), VII (1974), VIII (1978); Dollmetsch (1976): "Untersuchungen über die Ursachen der Agglomeration von Dispersionsfarbstoffen durch Farbstoffhilfsmittel beim Färben", Forschungsbericht Neue Serie No. 2, Institut für Chemiefasern der Institute für Textil- und Faserforschung Stuttgart; Leube (1978) Textil Praxis International, Heft 6, 733–737; Heft 7, 823–831.

The procedure in accordance with the present invention is particularly suitable for the qualitative and/or quantitative determination of an immunochemically reactive component, such as a hapten, antigen or antibody present in an aqueous test medium, but can also be employed for the histological or cytological determinations of such components.

For this reason the invention similarly relates to the new immunochemical reagents, consisting of an aqueous dispersion of particles of a hydrophobic dye or pigment, normally organic by nature, or polymeric nuclei coated with such a dye or pigment, to which either directly or indirectly an immunochemically reactive component has been attached.

The invention similarly relates to new test kits containing such an immunochemical reagent.

By coupling the immunochemically reactive component to the particle, directly or indirectly, we mean any chemical, physical or physico-chemical bonding, such as a chemical covalent bond, via hydrogen bridges, polar attraction, or adsorption including also biospecific adsorption.

The particles of the aqueous dispersion of a hydrophobic dye or pigment, or of polymeric nuclei coated with such a dye or pigment, have a particle size of at least 5 nm, and preferably from 10 to 500 nm. These dispersions are normally sols, but other types of dispersions can also occur.

The dye sol particles carry a charge, which gives a stabilising effect by mutual repulsion. By adding mainly strong electrolytes, the charge pattern is modified, so that aggregation and flocculation take place. This can be prevented by coating the particles with macromolecules which possess polar groups, such as proteins, polysaccharides, polyethyleneglycols, polyvinyl alcohols etc.

As protective proteins it is possible to use antigens, antibodies or polypeptide fragments thereof which are still immunochemically active. Furthermore it is possible to envisage haptens attached to macromolecules (e.g. proteins, polysaccharides) which during the pertinent immunoassay do not give rise to any interfering reaction with the other components. During this the dyestuff sol-labelled, immunochemically-active component is simultaneously obtained.

It may occur that, in order to stabilise the dyestuff sol, such a high concentration of, for example, antibody is required on the surface of the colloidal particles that the effective immunochemical activity of this immobilised protein is affected, for example by steric hindrance. In such a case the coating can be performed in two stages:

(1) coating with an optimum quantity, to be determined, of for example an antibody, followed by
(2) coating with a macromolecular compound (e.g. a protein, a polysaccharide, polyethyleneglycol, polyvinyl alcohol) which, during the pertinent immunoassay, does not give rise to an interfering reaction with the other components. This "subsequent coating", e.g. with bovine serum albumin, can at the same time serve to reduce possible non-specific adsorption effects.

Another possibility of a protective protein can be protein A or the group of lectins (e.g. Con A). After an initial coating of the sol particles with these proteins it is possible, due to the specific affinity of the said proteins, to apply a second layer selectively by adsorption of immunoglobulins (via the Fc part), and glycoproteins (also including immunoglobulins), via the sugar residue(s) present.

Another possibility is that the dyestuff sol particles are first coated by a polymer or co-polymer which is inert in the final immunoassay, after which subsequently by adsorption and/or covalent attachment, an immunochemically active component can be attached to the layer of coating material. During the coating of the sol particles by the inert polymer or co-polymer each particle can be enveloped separately, but it is also possible for several colloid particles to be included inside one and the same polymeric layer.

The covering of the dyestuff sol particles by the inert polymer can take place in two ways: by bringing the dyestuff sol in contact with the polymer, followed by adsorption and/or covalent attachment to the sol particles, or by bringing the sol into an environment of a monomer, or different monomers, and polymerising or co-polymerising the latter in situ. Polymerisation can be undertaken for example by radiation or by the addition of a suitable initiator, such as for example a persulphate. The envelopment of a dyestuff sol particle by in situ polymerisation of the monomeric solution, in which the particle is located, under the influence of an inorganic initiator such as a persulphate, involves practical difficulties, because the sol—when such an initiator is added—flocculates out. It was however established that such coating is nevertheless possible by first of all protecting the sol particles, and then placing the protected particles in the monomeric solution, polymerisation only being initiated subsequently. The compounds mentioned above can be employed as protective agents for this purpose.

Coating of the colloidal dyestuff particles with the following aim(s): stabilisation of the sol, the application of an immunochemically reactive component, elimination of non-specific adsorption effects, and/or the application of an intermediary polymer or co-polymer layer respectively, can be performed via direct/indirect adsorption at the colloidal dyestuff particles, but also by covalent chemical attachment. The latter is governed by the presence of suitable functional groups in the coating material and in the dyestuff. For example one can envisage the diazotization of aromatic amino groups followed by diazo attachment to an activated aromatic ring system; carboxyl groups can be activated by a carbodiimide and then, possibly via an active ester, be attached to a primary amino component. Aliphatic primary amino groups and hydroxyl groups can be activated for example by cyanogen bromide or halogen-substituted di- or tri-azines, after which attachment with a primary amino component or with for example a component containing a —SH, —OH or imidazolyl group can take place. Use can also be made of bifunctional reactive compounds. For example glutaraldehyde can be used for the mutual coupling of primary amino components, whilst for example a heterobifunctional reagent such as N-succinimidyl 3-(2-pyridyldithio) propionate can be employed for the coupling of a primary amino component to a component containing a thiol group.

In this context mention can also be made of the reactive dispersive-, and other reactive dyestuffs not soluble in water, where the dye consists of a chromophore covalently coupled with a group which as such is already reactive, such as for example halogen-substituted di- and triazines, epoxy groups, vinyl-sulphonic groups and dihaloquinoxalines (see Siegel, (1972) in: Venkataraman (Ed.): "The Chemistry of Synthetic Dyes", Academic Press, New York, Vol. VI; Harms, 1979 in: Banks (Ed.): "Organofluorine Chemicals and their Industrial Applications", Ellis Horwood Ltd., Chichester; pp. 188-204).

Usually the immunochemically reactive components labelled with colloidal dye particles are employed as reagent in combination with other reagents, for the detection and/or quantitative determination of for example haptens, antigens and antibodies, for which all types of immunochemical techniques can be considered such as those used for RIA and EIA.

Hence the invention also relates to "test kits" for use in such immunochemical techniques, which as their most important component contain an immunochemically reactive component labelled with a dyestuff sol, consisting of a dyestuff sol, the particles of which are coated directly or indirectly, adsorptively and/or covalently, with the immunochemically reactive component.

One of the conventional immunochemical techniques is competitive immunoassay, which can be used for the demonstration and/or determination of any immunochemically reactive component. For the demonstration, for example, of a certain antigen, this method consists of bringing a test sample, containing an unknown quantity of antigen, into contact either with a certain quantity of the corresponding antigen labelled with a dye sol and an antibody attached to an insoluble carrier, which is directed against this antigen, or a certain quantity of antigen attached to an insoluble carrier and an antibody labelled with a dyestuff sol directed against this antigen.

After the reaction has terminated the nature and/or the quantity of the dyestuff is determined in the bound and/or the free fraction, which provides a qualitative and/or quantitative indication for the antigen to be determined. Mutatis mutandis, an analogous procedure applies to the determination of other immunochemically reactive components.

Widespread use is also made of the "sandwich technique" which is also appropriate for use with immunochemically reactive components labelled with colloidal dyestuff particles. Using this technique such a component, e.g. an antibody in cases where an antigen has to be determined, is immobilised on an insoluble carrier material. This carrier material can for example be the interior surface of the reaction vessel in which the immunochemical reaction is performed; it is also possible to employ carrier materials in the form of beads or small rods. After initial incubation with the specimen containing the antigen, possibly followed by a washing step, a second incubation takes place with an antibody labelled with a dyestuff sol, after which the dyestuff is determined in the bound and/or the free phase.

Apart from the techniques mentioned for this purpose there are also innumerable other immunochemical techniques where the immunochemically reactive component labelled with the dyestuff sol can be employed as reagent. We are thinking here especially of an immunochemical test based on the agglutination principle. Here for example an antibody labelled with a dyestuff sol is added to a specimen of a liquid containing the antigen to be determined. The separation of the bound and free fractions of the labelled components can be dispensed with here, because the detection is based on a visual assessment of the dyestuff sol or on a spectrophotometric/colorimetric determination.

The present invention also renders it possible to demonstrate the presence in a test specimen of different immunochemically reactive components, such as for example haptens, antigens and antibodies or combinations thereof, simultaneously by employing, for each of the components to be demonstrated, a corresponding immunochemically reactive component which has been labelled with a colloidal dyestuff particle which is characteristic for that component.

Determination of the nature and/or the concentration of the dyestuff at the end of the test can be performed using various known techniques. As examples of these we can mention visual assessment which is excellently suitable for a qualitative determination precisely when employing dyestuffs; for quantitative determination use can for example be made of colorimetry-spectrophotometry. The said methods are also suitable for the ultimate detection in the agglutination test, where importance attaches not so much to the concentration of the dyestuff, but instead to the external appearance of the dyestuff sol (a greater or lesser degree of aggregation, possible flocculation, spectral modifications caused by this). Furthermore for the quantitative determination of the dyestuff (or dyestuffs, during simultaneous determination) thought can be given to fluorimetry and—in the case of metal complex dyestuffs and/or pigments, to "normal" and/or flameless atomic absorption spectrophotometry. The invention will now be described in greater detail with the aid of the following examples.

EXAMPLE 1

Colorimetric and/or visual determination of human chorionic gonadotropin (HCG) in accordance with the DIA principle described ("Sandwich test")

1.1 Preparation of the dye sol

Palanil$^R$ red BF (BASF, 7 g) was dispersed in distilled water (140 ml). The dispersion was stirred for 45 minutes at room temperature and then centrifuged (30 min., 125 g=1,225 N/kg). The supernatant was transferred into other centrifuge tubes and centrifuged (30 min., 7,500 g=73,500 N/kg). The supernatant was removed and the pellet was washed three times with distilled water (3×140 ml, centrifuge: 30 min., 7,500 g=73,500 N/kg). The pellet was resuspended in distilled water (70 ml), and subsequently so many glass beads (dia.=3 mm and dia.=4 mm, mixture 1:2) are added that the liquid level is the same as that of the beads. Then rolling was carried out for 5 days at room temperature on a roller bench. The liquid was decanted and centrifuged (30 min., 300 g=2,940 N/kg). The supernatant was then transferred into other centrifuge tubes and again centrifuged (30 min., 1,000 g=9,800 N/kg). From this last supernatant ¾ (52.5 ml) was carefully aspirated and this concentrated dyestuff sol was stored at room temperature. The extinction at 533 (=$\lambda$max) nm of a 20×diluted sample of this sol was 1.57.

1.2. Preparation of the rabbit anti-HCG immunoglobulin/dye sol conjugate

A sample (0.8 ml of the dye sol described in 1.1 above was diluted with distilled water (4.2 ml) and the pH was adjusted to 7.0 using 0.1 mol/l NaOH or HCl. The extinction of this sol is 5.0 at 533 nm (=$\lambda$max). Subsequently rabbit anti-HCG immunoglobulin solution (0.1 ml)* was added; the reaction mixture was shaken every 15 minutes during one hour at room temperature, after which a solution of bovine serum albumin (BSA) was added (1 ml; 307.2 g BSA+0.1 g sodium merthiolate+5 mmol NaCl/l, pH 7.0). The dispersion was shaken every 15 minutes during one hour at room temperature and was then centrifuged (30 min., 4000 g=39,200 N/kg). The supernatant was removed and the pellet was resuspended up to a volume of 5 ml in a solution having the following composition: 51.2 g BSA+0.1 g sodium merthiolate+5 mmol NaCl/l (pH adjusted to 7.0 with 0.1 mol/l NaOH).

*The solution of rabbit anti-HCG immunoglobulin was prepared as follows: The immunoglobulin fraction of rabbit anti-HCG serum was isolated via the known Na$_2$SO$_4$ precipitation method. The precipitate was dissolved in and dialysed against an aqueous solution of 5 mmol/l NaCl, the pH of which has been adjusted to 7.0 with solid Na$_2$CO$_3$. The dialysed solution was finally diluted to a protein concentration of 1 mg/ml (in accordance with the Warburg-Kalckar formula: protein concentration (mg/ml)=$1.45 \times A_{280}^{1\ cm} - 0.75 \times A_{260}^{1\ cm}$), or 0.65 mg/ml (according to $A_{280}^{1\ cm,\ 1\%}=14.5$ for IgG).

1.3. "Coating" of Microelisa ® plates with rabbit anti-HCG immunoglobulin

Phosphate buffer (FFB)

0.04 mol/l Na$_2$HPO$_4$ and 0.04 mol/l NaH$_2$PO$_4$ were mixed to give a solution with pH 7.4; then add NaCl up to a concentration of 0.15 mol/l.

Solution A

Rabbit anti-HCG immunoglobulin (see 1.2) dissolved in FFB up to a concentration of 30 mg/l.

Solution B 20 g BSA+0.1 g sodium merthiolate/l FFB.

Solution A (0.11 ml) was pipetted into the wells of Microelisa ® plates, after which the plates were incubated for 16 hours at 0°-4° C. After aspiration, solution B (0.11 ml) was added to all the wells, after which the plates were incubated for 30 minutes at room temperature. Finally the wells were aspirated and washed three times with distilled water, after which the plates were dried (16 hours at room temperature over pre-dried silica gel), packaged in aluminium laminate bags (with silica gel sachet) and stored at 4° C.

1.4. Determination of a standard curve for HCG in phosphate buffer and in blank urine Phosphate buffer (FFB)

As described in 1.3, but with 1 g BSA/l, and 1 g sodium merthiolate/l.

Washing buffer I

Phosphate buffer.

Washing buffer II 0.1 mol TRIS ((HOCH$_2$)$_3$CNH$_2$)+0.1 mol NaCl+0.5 g Tween ®-20+0.1 g sodium merthiolate/l, adjusted to pH 7.4 with 4 mol/l HCl.

Ethanol

P.A., 96% (v/v).

HCG

A solution of human chorionic gonadotropin with a content of 1,000 IU (immunoassay)/ml FFB.

Blank urine

Urine from non-pregnant women, filtered over Hyflo ® and subsequently frozen; prior to use filtered through folding filter.

Conjugate

The dye sol/anti-HCG conjugate, prepared as described in 1.2, (9 ml) was mixed with concentrated phosphate buffer (1 ml; 10×concentrated FFB).

Procedure

1. The following dilution series of the HCG solution were made in FFB and urine respectively: 4,000, 1,000, 250, 62.5, 15.6, 3.9 m IU (immunoassay)/ml.
2. Then, 0.1 ml of these solutions, and of blank FFB and urine, was pipetted into the wells of a Microelisa ® plate which has previously been "coated" as described in 1.3 with rabbit anti-HCG immunoglobulin (see 1.3). All this is done in duplicate.
3. Close the plate with a suitable cover, and incubate for 3.5 hours at 37° C. in an atmosphere saturated with water vapor.
4. Aspirate the wells, pipette wash buffer I (0.3 ml) into each well and aspirate again.
5. Pipette the conjugate (0.1 ml) into each well.
6. Incubate as described in item 3, but now for 18 hours.
7. Aspirate the wells, assess the color in the wells visually and/or pipette wash buffer II (0.3 ml) into the wells. Aspirate and repeat this procedure twice further.
8. Add ethanol (0.12 ml) to all the dry wells, shake gently and assess the colour by eye and/or measure the extinction at 516 nm (=$\lambda$max).

If, using the procedure described, samples having an unknown HCG content are also included, the HCG concentration can easily be estimated by eye; a more accurate determination can if required be performed by extinction measurement and comparison with the standard curve. Standard curves for HCG in urine and FFB determined in this manner are shown in FIG. 1.

The detection limit, defined as (blank+2×standard deviation) is for FFB 3.9 m IU (immunoassay)/ml, and for urine 15.6 IU (immunoassay)/ml.

1.5. Determination of HCG in the urine of women in order to detect pregnancy.
Reagents: see section 1.4.
Procedure:
As described in 1.4., but now with the inclusion of the corresponding urine specimens, which may or may not be diluted. The results are shown in the following table:

| Specimen | Dilution | Pregnosticon ® "All-in" | Visual | $A_{516}$ | HCG conc. |
|---|---|---|---|---|---|
| 1374 | Undiluted | + | + | 0.588 | 4000 |
| 1374 | 1:10 | + | + | 0.595 | 40000* |
| 1130 | Undiluted | + | + | 0.659 | 4000 |
| 305 | Undiluted | + | + | 0.707 | 4000 |
| 726 | Undiluted | − | − | 0.057 | 80 |
| 546 | Undiluted | − | − | 0.043 | 65 |
| 1123 | Undiluted | − | − | 0.047 | 65 |

*in the undiluted specimen.

The conclusion as to whether or not pregnancy exists corresponds with the results of the pregnancy test Pregnosticon ® "All-in". In this latter test "+"= ≧1000 IU/ml and "−"= ≦500 IU/l.

EXAMPLE 2

As Example 1, but disperse dye/anti-HCG conjugates were prepared using Resolin ® Brilliant Blue RRL and the fluorescent disperse dyes Samaron ® Brilliant Red H6GF, Samaron ® Brilliant Yellow H10GF, Palanil ® Luminous Red G and Palanil ® Luminous Yellow G as colloidal labels. (for corresponding $\mu$max values see Example 9).

Dilution series of HCG were made in buffer. Reduction of the incubation periods as compared to the standard procedure was investigated: HCG incubation 2.5 h and conjugate incubation 2.5 h instead of 6.5 and 18 h, respectively. A detection limit of 0.02–0.25 mIU HCG/ml was obtained. This compares very well with other test systems:
RIA: 2 mIU HCG/ml (DL:HCG concentration at (90% binding+2×SD))
EIA: 20 mIU HCG/ml (DL: as for RIA)
SPIA: 0.25–1 mIU/ml (DL: blanc+2×SD) (colorimetric detection)
rev-HAI: 10–20 mIU HCG/ml (DL: HCG concentration giving a significant change in pattern).

Additionally, the total test period was decreased from 24.5 h to 5 h, with only a limited effect on the detection limit (in the case of Samaron Brilliant Red H6GF).

The fluorescent disperse dyes were investigated in order to improve the detection limit by measuring fluorescence instead of absorbance. A significant improvement was obtained in the case of Samaron ® Brilliant Yellow H10GF and Palanil ® Luminous Yellow G, whereas no effect was found in the case of Samaron ® Brilliant Red H6GF and Palanil ® Luminous Red G.

EXAMPLE 3

DIA for Hepatitis B surface Antigen (HBsAg); sandwich system 3.1. Preparation of dye sol
See section 1.1.; the disperse dyes Palanil ® Red BF and Samaron ® Brilliant Red H6GF were used as colloidal labels. (for corresponding $\lambda$max values see Example 9).

3.2. Preparation of the sheep-(anti-HBsAg) IgG/dye conjugate
See section 1.2; but use sheep-(anti-HBsAg) immunoglobulin instead of rabbit anti-HCG IgG.

3.3. Coating of Microelisa ® plates with sheep-(anti-HBsAg) IgG.
See section 1.3.; use the sheep instead of the rabbit immunoglobulins.

3.4. Determination of standard curves for HBsAg (subtype ad and ay).
Dilution series of HBsAg (ad and ay) were made using human negative control serum as diluent, in the range 4–1000 ng/ml. Samples (0.1 ml) of these dilutions, and of the negative control serum, were assayed according to the procedure described in section 1.4. (steps 3–8); for $\lambda$max (ethanol) see Example 9.
Detection limits of 16–23 ng/ml (ad) and 24–38 ng/ml (ay) were obtained with the Samaron ® dye/conjugate. For comparison:
EIA (Hepanostika ®); 3 ng/ml
EIA (Hepanostika-T ®): 0.7 ng/ml (DL: mean negative value+5×SD)
SPIA: 20-40 ng/ml (DL: blank+2×SD) (colorimetric detection).

The DIA/sandwich system was also used to compare several samples of monoclonal antibodies, with a standard preparation of heterogeneous sheep anti-HBsAg IgG. Three samples gave dose response curves similar to the standard, whereas the other preparations were of a distinctly poorer quality.

EXAMPLE 4

DIA for Human Placental Lactogen (HPL); sandwich system 4.1. Preparation of dye sol
See section 1.1.; the disperse dyes Palanil ® Red BF and Palanil ® Yellow 3G were used as colloidal labels (for corresponding $\lambda$max values see Example 9).

4.2. Preparation of the rabbit (anti-HPL) IgG/dye conjugate
See section 1.2.; but use anti-HPL instead of anti-HCG.

4.3. Coating of Microelisa ® plates with rabbit anti-HPL IgG
See section 1.3.; but use anti-HPL instead of anti-HCG.

4.4. Determination of Standard curves for HPL
Dilution series of HPL were made in FFB (see section 1.4) in the range 0.4–100 ng/ml. Samples (0.1 ml) of these dilutions, and of FFB, were assayed according to the procedure described in section 1.4. (steps 3–8); for $\lambda$max (ethanol) see Example 9.

A detection limit of 1.2–1.7 ng HPL/ml was obtained. For comparison:
RIA: 0.03–0.14 ng/ml
EIA: 2 ng/ml
SPIA: 0.12 ng/ml (colorimetry).

EXAMPLE 5

DIA for anti-Rubella; sandwich system 5.1. Preparation of dye sol

See section 1.1; the disperse dyes Palanil ® Red BF and Resolin ® Brilliant Blue RRL were used as colloidal labels (for corresponding $\lambda$max values see Example 9).

5.2. Preparation of the sheep anti-(human IgG) IgG-/dye conjugate

See section 1.2; but use the sheep immunoglobulin instead of the rabbit material.

5.3. Coating of Microelisa ® plates with inactivated Rubella viral antigen (obtained from tissue culture)

See section 1.3.; but use the Rubella antigen instead of the immunoglobulin.

5.4. Determination of standard curves for human anti-Rubella

Dilution series of human anti-Rubella were made using sheep negative control serum as diluent, in the range 0.4–320 IU/ml. Samples (0.1 ml) of these dilutions, and of the negative control serum, were assayed according to the procedure described in section 1.4. (steps 3–8); for $\lambda$max (ethanol) see Example 9.

The detection limit, defined as (BL+2×SD), was 2.5 IU/ml, which compares favorably with an estimation of the detection limit of Rubenostika of ~10 IU/ml.

EXAMPLE 6

DIA for human Prolactin (PRL); sandwich system 6.1. Preparation of dye sol

See section 1.1.; the disperse dyes Palanil ® Luminous Red G and Palanil ® Luminous Yellow G were used as colloidal labels (for corresponding $\lambda$max values, see Example 9).

6.2. Preparation of the monoclonal (anti-PRL) IgG/dye conjugate

See section 1.2; but use the monoclonal IgG instead of the rabbit material.

6.3. Coating of the Microelisa ® plates/strips with monoclonal (anti-PRL)IgG

See section 1.3.; but use the monoclonal IgG instead of the rabbit material.

NOTE: Immunoglobulins from *different* clones were used for the preparation of the conjugate (6.2.) and for the coating of the plates/strips.

6.4. Determination of standard curves for PRL

Dilution series of PRL were made in FFB (see section 1.4.) in the range 0.4–100 ng/ml. Samples (0.2 ml) of these dilutions, and of FFB, were assayed according to the procedure described in section 1.4. (steps 3–8), with the following modifications:
  incubation of antigen (PRL): 20 h, room temperature
  incubation of conjugate: 20 h, room temperature.
  For $\lambda$max (ethanol) see Example 9.

A detection limit of 1–4 ng/ml was obtained. For comparison:

EIA 1–4 ng/ml
SPIA 6–10 ng/ml.

EXAMPLE 7

Simultaneous determination of HCG and HPL, according to the DIA principle; sandwich system 7.1. Preparation of the dye sols See section 1.1; the disperse dyes Resolin ® Brilliant Blue RRL and Palanil ® Yellow 3G, were used as colloidal labels (for corresponding $\lambda$max values see Example 9).

7.2. Preparation of the rabbit (anti-HCG) IgG/- and rabbit (anti-HPL) IgG/dye conjugates See section 1.2.; prepare the following combinations:
Resolin ® Brilliant Blue RRL/anti-HCG
Palanil ® Yellow 3G/anti-HPL.

The combined conjugate is prepared by mixing equal volumes of the two conjugates, yielding a final absorbance of 5 (at $\lambda$max) for each dye-conjugate.

7.3. Coating of Microelisa ® plates with rabbit anti-HCG, rabbit anti-HPL, and with a mixture of both See section 1.3.; plates for the simultaneous assay were prepared using the following coating mixture:
rabbit anti-HCG 15 ng/l
rabbit anti-HPL 15 ng/l.

7.4. Simultaneous determination of HCG and HPL

Generally, the assay procedure described in section 1.4. was used (for $\lambda$max values in ethanol, see Example 9):

(a) The single and combined conjugates were tested in microtitre plates which were coated only with rabbit anti-HCG or anti-HPL. The combined conjugate and the anti-HCG conjugate gave an equal response in a dilution series of HCG in FFB (see section 1.4), whereas the anti-HPL conjugate did not react. The anti-HPL conjugate gave a higher response than the combined conjugate in a dilution series of HPL in FFB, whereas the anti-HCG conjugate did not react.

Figure 2:
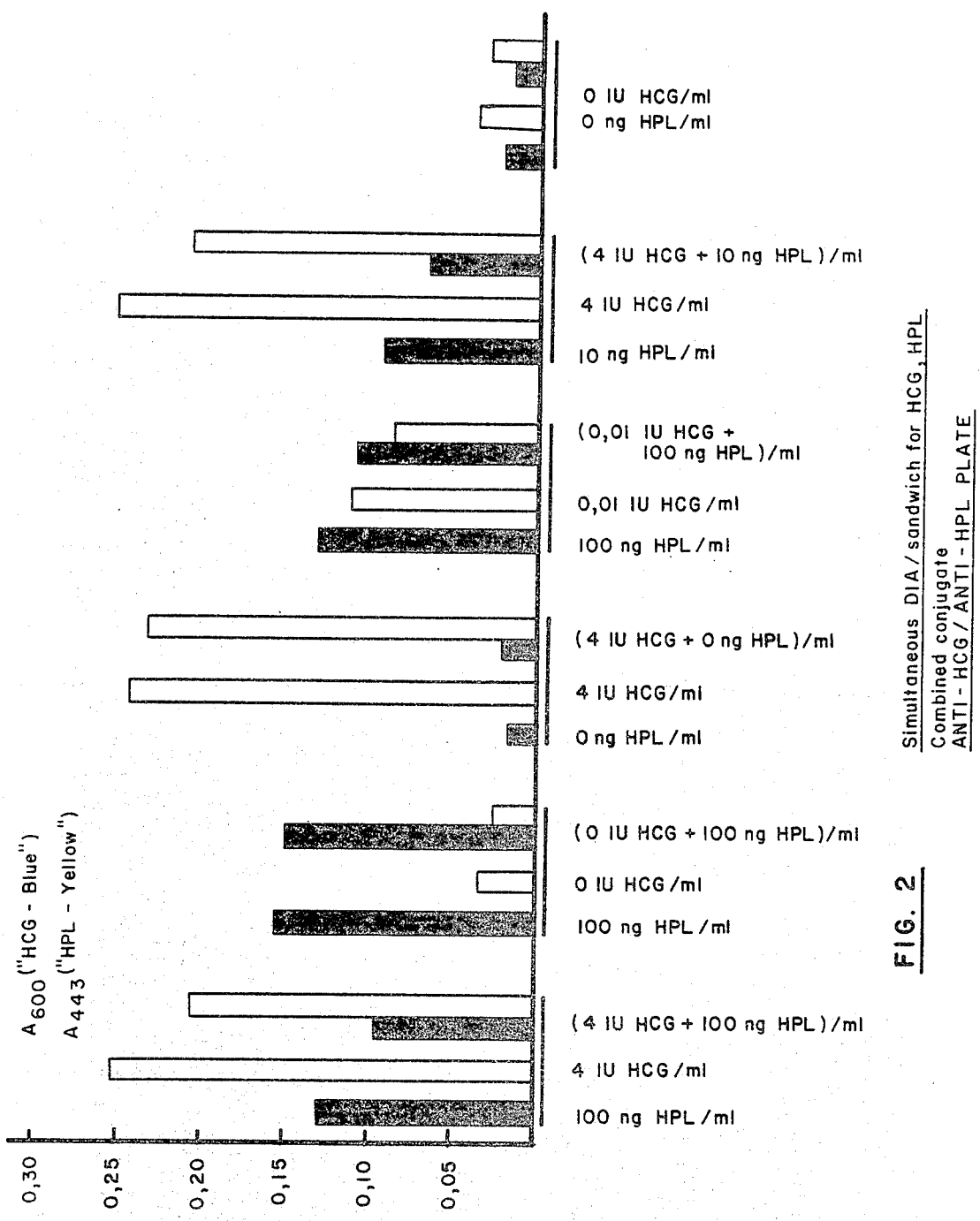

(b) Finally, samples of HCG, HPL and (HCG+HPL) in FFB were incubated in the wells of a microtitre plate coated with rabbit anti-HCG and anti-HPL simultaneously. The second incubation was performed with the combined conjugate. The results are presented in FIG. 2, which demonstrates the possibility of a simultaneous DIA/sandwich.

EXAMPLE 8

DIA for testosterone 8.1. Method 1

This method is based on the detection of free anti-testosterone on the solid phase, after incubation with the testosterone containing sample.

8.1.1. Preparation of the dye sol

See section 1.1.

8.1.2. Preparation of testosterone-11α-hemisuccinyl-BSA/dye sol conjugate

Testosterone-11α-hemisuccinate is dissolved in 2 ml dimethylformamide (DMF) and then the solution is cooled to −15° C.

Bovine serum albumin (BSA, 140 mg) is dissolved in distilled water (3 ml), after which 40 μl of 4 mol/l NaOH and 2 ml DMF is added. The solution is then cooled to −15° C.

Now 12.5 μl of N-methylmorpholine and 12.5 μl of isobutyl chloroformate is added to the solution of testosterone derivative. After three minutes this reaction mixture is added to the BSA solution. While stirring is taking place the reaction mixture is held for 1 hour at −15° C. and then for 3 hours at 0° C. Then the reaction mixture is dialysed against distilled water for 16 hours at 4° C., with the distilled water being regularly renewed. The dialysed solution is then centrifuged and the clear supernatant is freeze-dried.

The testosterone-11α-hemisuccinyl-BSA/dye sol conjugate is now prepared using the method described for the immobilisation of rabbit anti-HCG immunoglobulin on a Palanil® Red BF sol while using the same concentration for the testosterone-BSA derivate as for the rabbit anti-HCG immunoglobulin.

8.1.3. "Coating" of Microelisa® plates with rabbit anti-testosterone immunoglobulins The coating was carried out as described in section 1.3. using the immunoglobulin fraction isolated from a rabbit antiserum, obtained by immunisation with testosterone-11α-hemisuccinyl-BSA.

8.1.4. Determination of testosterone

Using the reagents and the test procedure as described for HCG in section 1.4., a standard curve was determined for testosterone by means of which subsequently the testosterone concentration of unknown samples was calculated via the $A_{516}$ of the samples, obtained in accordance with the said test procedure. The detection limit of this determination is 1 ng/ml. It is easy to estimate the testosterone contents by reading with the naked eye (comparison of the color intensity of standard and unknown samples after stopping the reaction.

8.2. Method 2

This method is based on a competitive binding of testosterone (T) and $T^3$-BSA to anti-($T^{11}$-BSA), which was immobilized onto the solid phase (e.g. polystyrene tube, or micro titre plate).

Detection followed by a second incubation with an anti-($T^{11}$-BSA)/dye conjugate.

NOTE:
  $T^3$-BSA: testosterone-3-O-carboxymethyloxime, covalently coupled to a $NH_2$-function of BSA (amide bond)
  $T^{11}$-BSA: testosterone-11-hemisuccinate, covalently coupled to a $NH_2$ function of BSA (amide bond).

8.2.1. Preparation of dye sol

See section 1.1; the disperse dyes Samaron® Brilliant Red H6GF and Samaron® Brilliant Yellow H10GF were used as colloidal labels (for corresponding $\lambda$max values, see Example 9).

8.2.2. Preparation of the rabbit (anti-$T^{11}$-BSA) IgG/dye conjugate

See section 1.2.; but use the rabbit anti-$T^{11}$-BSA instead of anti-HCG.

8.2.3. Coating of Microelisa® plates and polystyrene tubes with rabbit (anti-$T^{11}$-BSA) IgG See section 1.3.; but use the rabbit (anti-$T^{11}$-BSA) instead of the anti-HCG.

NOTE: 1 ml of solutions A and B are used in case of coating of the tubes.

8.2.4. Determination of standard curves for testosterone

Solutions of T and $T^3$-BSA were made in FFB (see section 1.4.).

(a) The concentration of $T^3$-BSA to be used in the competitive assay, was investigated by incubation of a dilution series of $T^3$-BSA only, followed by the conjugate; 1 ml volumes per tube, or 0.1 ml volumes per microtitre plate well. Procedure as described in section 1.4. (steps 3–8): for $\lambda$max (ethanol) see Example 9. For the total competitive assay concentrations of $T^3$-BSA corresponding with 2 and 16 pmol T/ml total test volume, were choosen.

(b) The competitive assay was performed using constant concentrations of $T^3$-BSA corresponding with 2 and 16 pmol T/ml total test volume, and a dilution series of 0–64 pmol T/ml sample; for the tubes: 0.9 ml of testosterone containing sample and 0.1 ml of a $T^3$-BSA solution (corresponding with 20, respectively, 160 pmol T/ml); for the microtitre plate the respective volume are changed to 0.09 and 0.01 ml. Further procedure as described in section 1.4. (steps 3–8); for $\lambda$max (ethanol) see Example 9.

The detection limit, defined as (BL−2×SD), was 0.2–0.4 pmol T/ml sample, using a $T^3$-BSA concentration corresponding with 2 pmol T/ml total test volume. The total detection range was about 0–8 pmol T/ml sample. In RIA and EIA, 50% binding is reached at, respectively, 1 pmol T/ml and 0.7 pmol T/ml.

EXAMPLE 9

Alternative methods for the preparation of dye sols 9.1. Disperse dyes

Instead of the Palanil® Red BF (BASF) mentioned in section 1.1., other disperse dyes have also been used for preparing dyestuff sols, including:

| | | $\lambda_{max}(nm)$ | | $\lambda_{measuring}(nm)$[c] |
|---|---|---|---|---|
| | | water[a] | ethanol[b] | ethanol |
| Palanil® Violet 6R | BASF | 623 | 571 | — |
| Palanil® Yellow 3G | BASF | 415 | 443 | 443 |
| Palanil® Luminous Yellow G[d] | BASF | 496 | 464 | 443 |
| Palanil® Luminous Red G[d] | BASF | 520 | 544 | 540 |
| Terasil® Brilliant Flavin 8GFF[d] | Ciba-Geigy | 488 | 461 | 443 |
| Terasil® Brilliant Pink 4BN | Ciba Geigy | 571 | 571 | 540 |
| Cibacet® Violet 2R | Ciba-Geigy | 538 | 592 | 549 |
| Foron® Brilliant Flavin S8GF[d] | Sandoz | 433 | 427 | — |
| Resolin® Brilliant Blue RRL | Bayer | 670 | 578 | 600 |
| Procinyl® Blue R[e] | ICI | 672 | — | — |
| Samaron® Brilliant Red H6GF[d] | Hoechst | 512 | 510 | 510 |
| Samaron® Brilliant Yellow H10GF[d] | Hoechst | 451 | 458 | 443 |
| Samaron® Brilliant Orange HFR[d] | Hoechst | 508 | 499 | 492 |
| Samaron® | | | | |

-continued

| | | $\lambda_{max}(nm)$ | | $\lambda_{measuring}(nm)^{(c)}$ |
| --- | --- | --- | --- | --- |
| | | water$^{(a)}$ | ethanol$^{(b)}$ | ethanol |
| Violet HFRL | Hoechst | 566 | 543 | 540 |

$^{(a)}$as colloidal solution
$^{(b)}$as molecular solution
$^{(c)}$these values were used, due to the presently available filters
$^{(d)}$representatives of disperse dyes which can also be detected by flouorometry
$^{(e)}$representative of "reactive" disperse dyes.

Sols were prepared from the commercial dyestuffs, starting with a 5% (w/v) dispersion of the dyestuff in distilled water, in case of dry, powdered products; in case of liquid preparations experiments were started with a 5% (v/v) dispersion in distilled water.

Fractionation of the dye dispersion in water was carried out by centrifuging as described in 1.1. Fractionation to particle size has also been carried out with the aid of filters having a defined pore size; in this way usable sols are obtained, but the yield of dyestuff was considerably less than with centrifuging; furthermore the method is extremely time-consuming.

Hydrodynamic chromatography and the use of gradients during centrifuging form a useful supplement to the methods mentioned above.

9.2. Transfer dyes

Transfer dyes are dyes which are used during transfer printing, whereby a colored pattern is transferred from one surface to another, generally from paper to textile. The "sublistatic-, sublimation-, dry heat-, or thermoprinting process" makes use of sublimable organic dyes which are generally insoluble in water and soluble in organic environments. Sols of this type of dye have also been made up in water, via the "condensation method" (see J. Th. G. Overbeek in: H. R. Kruyt (Ed.) "Colloid Science", Vol. I, pp. 59-60; 1952, Elsevier, Amsterdam).

9.2.1. Lurafix ® Blue FFR (BASF)

Solutions (1 ml) of Lurafix ® Blue FFR in acetone with the following concentrations: 2, 1.5, 1.0, 0.8, 0.6, 0.4, and 0.2 g/l were added, during intensive stirring, always to 49 ml distilled water. The suspensions obtained are centrifuged (30 minutes, 1,000 g=9,800 N/kg) and the pellets are washed with distilled water (50 ml) and again centrifuged under the above-mentioned conditions. Then the pellets are suspended in such a volume of distilled water that the final concentration is 0.1 mg/ml. The final dye sols were obtained by subjecting the various suspensions to an ultrasonic treatment (Branson Sonifier B-12, 2 minutes, 70 Watts). The absorption spectrum of these dye sols was recorded in the region 750-360 nm. The value of $\lambda$max dropped from 716 to 617 nm, starting from the sol corresponding to an original dye/acetone concentration of 2 g/l down to 0.2 g/l. These spectral changes ae indicative of a decreasing particle size(see H. R. Kruyt: "Colloids", P.132; 1930, Wiley, New York; G. H. Jonker in H. R. Kruyt (Ed.): "Colloid Science", Vol. I, p. 102; 1952, Elsevier, Amsterdam; F. B. Gribnau, Dissertation, Utrecht 1935).

9.2.2. Lurafix ® Red BF (BASF)

a. A solution of Lurafix ® Red BF in acetone (1 ml, 0.5 g/l) is added, under vigorous stirring, to distilled water (24 ml). Then, under vacuum and at room temperature, the acetone is gently evaporated. Via an initially stable sol we finally get a precipitate. The suspension is centrifuged (30 minutes, 1,000 g=9,800 N/kg) and the pellet is resuspended in distilled water (25 ml) followed by an ultrasonic treatment (Branson Sonifier B-12, 2 minutes, 70 Watts).

b. A solution of Lurafix ® Red BF in acetone (1 ml, 5 g/l) is added under vigorous stirring to distilled water (249 ml, 50° C.). After 1 minute at 50° C. the mixture is cooled down to room temperature. After standing for one day at room temperature the initially stable sol starts to partially flocculate.

Photographs were taken of both freshly prepared sols by means of a scanning electron microscope, see FIGS. 5 and 6.

9.3. Fat dyes (solvent dyes)

A group of hydrophobic organic dyes which are insoluble in water but soluble in organic solvents or mixtures thereof. Using condensation methods as described in 9.2, sols can be made from these dyes in aqueous media.

9.4. Vat dyes

These water-insoluble anthraquinoid or indigoid dyes can be converted by reduction in alkaline medium into the corresponding, water-soluble leuco compounds. From these it is then possible to prepare dye sols by controlled oxidation. The leuco compounds (solubilised vat dyes) stabilised as sulphate ester can also be used for this purpose.

9.5. Organic pigments

These compounds which by definition are insoluble in water and organic media can be converted via a dispersion method (see P. Nylen and E. Sunderland: "Modern Surface Coatings", Interscience Publishers, London 1965) into colloidal "solutions".

EXAMPLE 10

Variations on the preparation of dye sol/immunoglobulin conjugates, as described in Example 1 (1.2.)

10.1. Immobilisation of immunoglobulin on colloidal dye particles 10.1.1. Lurafix ® Blue FFR (BASF)

A solution of Lurafix ® Blue FFR in acetone (5 ml, 1 g/l) is added under vigorous stirring to distilled water (245 ml). After centrifuging (30 minutes, 1,000 g=9,800 N/kg) the supernatant is removed and the pellet is washed with distilled water (50 ml). The pellet is resuspended in distilled water (up to 50 ml) and the suspension is treated ultrasonically (Branson Sonifier B-12, 2 minutes, 70 Watt). The sol obtained is diluted to give a $A_{617}^1$ cm of 1.0.

Rabbit anti-HCG immunoglubulin solution (0.2 ml, 1 mg/ml in a solution of 5 mmol NaCl/l, pH 7.0) is added to 10 ml of this sol and the mixture is stored for 16 hours at room temperature. Then a solution of Carbowax ®-20 M (0.2 ml, 10 g/l in a solution of 5 mmol NaCl/l, pH 7.0) is added and after being kept for 30 minutes at room temperature the sol is centrifuged (30 min. 4000 g=39,200 N/kg). The pellet is washed twice with a Carbowax ®-20 M solution (0.2 g/l in a solution of 5 mmol NaCl/l, pH 7.0) and subsequently resuspended therein to give an end volume of 5 ml.

The procedure described above is repeated, but now using normal rabbit immunoglobulin. The immunoactivity of the conjugates is established in the following manner:

Specimens (2 ml) of each conjugate are diluted using the latter-mentioned Carbowax®-20 M solution. To this 0.1 ml of a solution of HCG labelled with horseradish peroxidase HRP is added, and the reaction mixture is incubated for two hours at room temperature. Then this is centrifuged (30 mins., 4,000 g=39,200 N/kg), the pellets are washed twice with the latter-mentioned Carbowax®-20 M solution and resuspended in a solution of chromogen/substrate (o-phenylene-diamine/urea peroxide). After one hour at room temperature the enzyme reaction is stopped with 4 mol/l sulphuric acid, and the $A_{492}$ of the supernatants is measured after centrifuging (30 mins., 4,000 g=39,200 N/kg).

Dye/anti-HCG Ig conjugate: $A_{492}$=0.556
Dye/normal Ig conjugate: $A_{492}$=0.275.

10.1.2. Palanil® Red BF (BASF)

Immobilisation of for example proteins on solid carrier materials can be obtained via adsorption and via, direct or indirect, covalent coupling. The latter depends on the presence of suitable functional groups in the chemical structure of the dye. For example it is possible to use aromatic amino groups in a diazo coupling, while carboxyl groups can be activated by means of a carbodiimide. Aliphatic primary amino groups and hydroxyl groups can be activated by means of cyanogen bromide. Use can also be made of bi-functional compounds; thus it is possible to use glutaraldehyde for the coupling of amino components.

It is also possible in this context to use reactive dispersion dyes, these being dyes in which the chromphore is attached to a group which is already reactive as such, e.g. halotriazines and halo-pyrimidines.

The following examples have been performed with the dispersion dye Palanil® Red BF (BASF) using a fraction which was isolated in the following manner:

A dispersion of this dye in water (62.5 g/l) is centrifuged (30 min., 750 g=7,350 N/kg). The pellet is washed five times with distilled water and twice with a solution of poly (vinyl alcohol) (PVA) in water (1 g PVA/l; PVA: Mowiol® 28-99, Hoechst). Finally the pellet is resuspended to a final volume of 2 l in a PVA solution (0.1 g PVA/l in a solution of 5 mmol NaCl/l, pH 7.0). Samples (25 ml) of this dye sol, optionally after processing as described in greater detail in the following, were mixed with a solution of sheep anti-HCG immunoglobulin (0.65 ml, 40 mg/ml in a solution of 5 mmol NaCl/l, pH 7.0).

Adsorption and/or attachment of the protein to the colloidal dye particles was carried out for 16 hours under the specified conditions:

10.1.2.1. Adsorption
a. Adsorption at pH 4.0 and 0 mol NaCl/l
b. Adsorption at pH 4.0 and 0.1 mol NaCl/l
c. Adsorption at pH 7.0 and 0 mol NaCl/l
d. Adsorption at pH 7.0 and 0.1 mol NaCl/l
e. Adsorption at pH 6.0 and 0 mol NaCl/l (sol and protein were mixed at pH 4.0)
f. Adsorption at pH 6.0 and 0.1 mol NaCl/l (sol and protein were mixed at pH 4.0).

10.1.2.2. Diazo coupling

The dye was diazotised at 4° C. using $NaNO_2$/HCl and subsequently the pH of the reaction mixture was adjusted to 8.6 using solid $Na_2CO_3$. Finally protein was added; the coupling was performed at 4° C.

a. $NaNO_2$: 0.1 mol/l HCl: 0.1 mol/l
b. $NaNO_2$: 0.05 mol/l HCl: 0.05 mol/l
c. $NaNO_2$: 0.01 mol/l HCl: 0.01 mol/l 10.1.2.3. Cross-linking by means of glutaraldehyde The glutaraldehyde concentration of the dye sol was set at 1 and 10 mmol/l respectively, after which the pH was adjusted to 7.4 and 10.0 respectively. After 1 hour at room temperature the pH 10 was reduced to 9.0. Finally protein was added. The reaction was performed at room temperature.

a. Glutaraldehyde: 1 mol/l pH 7.4
b. Glutaraldehyde: 10 mmol/l pH 7.4
c. Glutaraldehyde: 1 mmol/l pH 10.0

10.1.2.4. CNBr activation

The dye sol was centrifuged and the pellet was washed with a solution of 5 mmol NaCl/l, pH 7.0. This was followed by resuspension in the same solution, or in a solution of PVA (10 g/l in a solution of 5 mmol NaCl/l, pH 7.0). The CNBr concentration of the various sols was adjusted to 0.045 and 0.005 mol/l respectively, after which the pH was adjusted to 11.0 using 4 mol/l NaOH. After 12.5 min. at room temperature the reaction mixtures were centrifuged and the pellets were washed twice with 0.1 mol/l $NaHCO_3$, pH 8.5 (4° C.). This was followed by resuspension to the initial volume in 0.025 mol/l $NaHCO_3$, pH 8.5. The protein coupling was performed at 4° C.

a. PVA concentration: 0 g/l CNBr conc.: 0.045 mol/l
b. PVA concentration: 10 g/l CNBr conc.: 0.045 mol/l
c. PVA concentration: 10 g/l CNBr conc.: 0.005 mol/l After 16 hours, the various reaction mixtures were centrifuged (30 min., 1,000 g=9,800 N/kg). The supernatants were removed and the pellets were washed twice with a solution of 5 mmol NaCl/l, pH 7.0 and resuspended to a final volume of 20 ml in the same solution.

The immuno-activity of the various conjugates was determined by incubating 5 ml of each conjugate (16 hours, 4° C., in the dark) with HCG, labelled with horseradish peroxidase (HRP). Then the reaction mixtures are centrifuged (1,000 g=9,800 N/kg, 30 min.). The pellets are washed twice with 3 ml of a solution of 5 mmol NaCl/l, pH 7.0 and subsequently re-suspended in a solution of chromogen/substrate (o-phenylenediamine/urea peroxide). After one hour reaction time at room temperature (in the dark) the enzyme reaction is stopped with 4 mol/l sulphuric acid and after centrifuging (30 min., 1000 g=9,800 N/kg) the $A_{492}$ of the supernatants is measured.

The above-mentioned procedure was also performed using HRP alone, to check specificity.

| Conjugate | $A_{492}$ (HCG-HRP) | $A_{492}$ (HRP)* | $A_{492}$ (HCG-HRP)** |
|---|---|---|---|
| 10.1.2.1-a. | 0.195 | 0.094 | |
| b. | 0.420 | 0.098 | 0.750 |
| c. | 1.738 | 0.109 | 1.970 |
| d. | 0.942 | 0.109 | 1.280 |
| e. | 0.230 | 0.109 | |
| f. | 1.129 | 0.103 | 1.496 |
| 10.1.2.2-a. | 0.738 | 0.120 | 1.260 |
| b. | 0.568 | 0.113 | 1.316 |
| c. | 0.777 | 0.086 | 1.505 |
| 10.1.2.3-a. | 1.097 | 0.062 | 1.920 |
| b. | 0.489 | 0.073 | |
| c. | 0.443 | 0.065 | |
| d. | 0.436 | 0.118 | |
| 10.1.2.4-a. | 1.900 | 0.088 | 2.153 |
| b. | 1.300 | 0.137 | 2.020 |

-continued

| Conjugate | $A_{492}$ (HCG-HRP) | $A_{492}$ (HRP)* | $A_{492}$ (HCG-HRP)** |
|---|---|---|---|
| c. | 1.022 | 0.118 | 1.671 |

*The conjugates were tested on three different days:
Day 1: 10.1.2.1-a/f
Day 2: 10.1.2.2-a/c and 10.1.2.3-a/c
Day 3: 10.1.2.4-a/c
**These conjugates were tested on the same day.

10.2. The effect of "subsequent coating" of dye sol/immunoglobulin conjugates on immuno-activity The experiments were performed using as example Palanil ® Red BF (BASF), using the type of sol already prepared in accordance with the method described in 1.1. above. This sol was adjusted to pH 7.0 using 0.1 mol/l NaOH or HCl and the extinction (at 533 nm) was set at 5.0.

Samples (37 ml) of this sol are mixed with a solution of rabbit anti-HCG immunoglobulin (0.74 ml, 1 g/l in a solution of 5 mmol NaCl/l, pH 7.0). The Ig concentration in the reaction mixture is then 20 mg/l. After 1 hour incubation at room temperature the following are added to the sols:
a. Nothing
b. Carbowax ®-20 M up to a concentration of 0.2 g/l
c. BSA up to a concentration of 0.2 g/l.

After a further 1 hour incubation at room temperature the sols are centrifuged (30 min., 4,000 g=39,200 N/kg). The pellets are re-suspended to a final volume of 37 ml in a solution of 5 mmol NaCl/l with either no extra additive, 0.2 g Carbowax ®-20 M/l, or 0.2 g BSA/l.

The various conjugates and the blank dye sol were tested in a DIA ("Sandwich test") using the procedure described in section 1.4. The dilution series for HCG employed was 0, 250, 1,000 and 4,000 IU (immunoassay)/l phosphate buffer.

| Conjugate | $A_{516}$ | | | |
|---|---|---|---|---|
| HCG (IU/l) | 0 | 250 | 1000 | 4000 |
| 10.2-a | 0.579 | 0.773 | 0.722 | 0.480 |
| b | 0.165 | 0.178 | 0.165 | 0.166 |
| c | 0.621 | 0.967 | 1.300 | 1.591 |
| Blank dye sol | 0.056 | — | — | — |

10.3. Purification methods for isolation of the conjugate after preparation

Inter alia the following techniques can be considered as methods of purification:
centrifugation
gel chromatography
affinity chromatography
membrane filtration
partial precipitation (flocculation, followed by washing and reconstitution of the sol).

Centrifugation and gel chromatography were investigated in detail and the results were compared with those for a conjugate which had not been purified but otherwise identically prepared. For this purpose we used non-purified conjugate 10.2-c.

10.3-a Gel chromatography 4 ml conjugate ($A_{533}^{1\ cm}=5.0$) is passed through a Sepharose ® CL 2B column (Pharmacia K 16/20, bed volume 35 ml; equilibrated with a solution of 5 mmol NaCl+0.2 g BSA+1.0 g NaN$_3$/l, pH 7.0). The column is eluated with equilibration buffer (room temperature, 30 ml/hour); detection of the eluate by measuring the $A_{280}$. Fractions of 1.3 ml are collected; the main fractions from the dye peak are mixed.

10.3-b Centrifugation 4 ml conjugate ($A_{533}^{1\ cm}=5.0$) is centrifuged (30 min., 4,000 g=39,200 N/kg) and re-suspended to give a final volume of 4 ml using a solution of 5 mmol NaCl+0.2 g BSA+1.0 g NaN$_3$/l, pH 7.0.

10.3-c No purification

The unpurified conjugate 10.2-c is used for this purpose.

The three conjugates are tested in a DIA (Sandwich test) using the procedure described in section 1.4. The HCG dilution series in section 10.2. was employed.

| Conjugate | $A_{516}$ | | | | |
|---|---|---|---|---|---|
| HCG (IU/l) | 0 | 250 | 1000 | 4000 | Yield (%) |
| 10.3-a | 0.228 | 0.551 | 0.713 | 0.505 | 4.3 |
| b | 0.218 | 0.339 | 0.456 | 0.557 | 93.6 |
| c | 0.234 | 0.418 | 0.583 | 0.700 | 100.0 |

10.4. Effect of the immunoglobulin concentration used during the preparation of the conjugate on the final immuno-activity Samples (5 ml) of a dye sol prepared from Palanil ® Red BF (BASF) in accordance with the method described in section 1.1. are mixed with 0.1 ml of a rabbit anti-HCG immunoglobulin solution (5 mmol NaCl/l, pH 7.0) resulting in final concentrations of:
10.4-a 10 mg/l
10.4-b 20 mg/l
10.4-c 40 mg/l
10.4-d 80 mg/l After incubation for one hour at room temperature, 0.1 mol of a BSA solution (5 mmol NaCl+20 g BSA/l, pH 7.0) is added, resulting in a final concentration of 0.4 g BSA/l. After incubation for 1 hour at room temperature the sols are centrifuged (30 min., 4,000 g=39,200 N/kg), the supernatants are removed and the pellets are re-suspended up to a final volume of 5 ml using a solution of 5 mmol NaCl+0.4 g BSA+0.1 g sodium merthiolate/l, pH 7.0.

The immuno-activity of the conjugates is ascertained by a DIA (Sandwich test) in accordance with the procedure described in section 1.4.; the HCG dilution series from section 10.2. was employed.

| Conjugate | $A_{516}$ | | | |
|---|---|---|---|---|
| HCG (IU/l) | 0 | 250 | 1000 | 4000 |
| 10.4-a | 0.268 | 0.499 | 0.761 | 1.000 |
| b | 0.362 | 0.658 | 0.902 | 1.141 |
| c | 0.511 | 0.741 | 0.913 | 1.107 |
| d | 0.507 | 0.681 | 0.847 | 0.955 |

10.5. Effect of the type of anti-HCG immunoglobulin on the immuno-activity of the conjugate; the use of anti-HCG immunoglobulin isolated from sheep and rabbit anti-HCG serum and of monoclonal mouse anti-HCG immunoglobulin The anti-HCG immunoglobulin/dye sol conjugates were prepared by coating samples (5 ml, $A_{533}^{1\ cm}=5.0$) of a Palanil ® Red BF sol, made in accordance with the method described in section 1.1., in the following manner:

10.5-a Sheep anti-HCG immunoglobulin

The protein solution (0.1 ml, 1 g/l in a solution of 5 mmol NaCl/l, pH 7.0) is added to the sol and the reaction mixture is incubated for 1 hour at room temperature. Then a BSA solution (0.1 ml, 20 g/l in a solution of 5 mmol NaCl/l, pH 7.0) is added and after incubation for 1 hour at room temperature the sol is centrifuged (30 min., 4,000 g=39,200 N/kg). The supernatant is removed and the pellet is re-suspended up to a final volume of 5 ml in a solution of 5 mmol NaCl+0.4 g BSA+0.1 g sodium merthiolate/l, pH 7.0.

10.5-b Rabbit anti-HCG immunoglobulin

The same as 10.5-a, but now with the rabbit immunoglobulin.

10.5-c Monoclonal mouse anti-HCG immunoglobulin

As 10.5-a, but now with the mouse immunoglobulin and using the following quantities:

10.5-c-1: 0.1 ml immunoglobulin solution (1 g/l, 5 mmol NaCl/l, pH 7.0)

10.5-c-2: 0.1 ml immunoglobulin solution (0.25 g/l, 5 mmol NaCl/l, pH 7.0).

The immuno-activity of the conjugates was ascertained using a DIA (Sandwich test) in accordance with the procedure described in section 1.4. The following HCG dilution series was used: 0, 15.6, 62.5, 250, 1,000 and 4,000 IU (immunoassay)/l.

| Conjugate HCG (IU/l) | $A_{516}$ | | | | | |
|---|---|---|---|---|---|---|
| | 0 | 15.6 | 62.5 | 250 | 1000 | 4000 |
| 10.5-a | 0.483 | 0.509 | 0.552 | 0.618 | 0.789 | 1.032 |
| b | 0.556 | 0.608 | 0.649 | 0.710 | 0.877 | 1.114 |
| c-1 | 0.406 | 0.432 | 0.450 | 0.503 | 0.536 | 0.586 |
| c-2 | 0.437 | 0.495 | 0.497 | 0.528 | 0.559 | 0.653 |

10.6. Effect of the BSA concentration offered during "subsequent coating" on the immuno-activity of the conjugate Conjugates of the dispersion dye Palanil ® Red BF (BASF) were made in accordance with the procedure described in sections 1.1. and 1.2., with however the following variations in the BSA concentrations:

| | BSA conc. in the added solution (g/l) | BSA conc. in the reaction mixture (g/l) |
|---|---|---|
| 10.6-a | 9.6 | 1.6 |
| b | 19.2 | 3.2 |
| c | 38.4 | 6.4 |
| d | 76.8 | 12.8 |
| e | 153.6 | 25.6 |
| f | 307.2 | 51.2 |

The conjugates were isolated as described in section 1.2. and finally re-suspended in a solution having the following composition: 5 mmol NaCl+0.1 g sodium merthiolate+x g BSA/l (pH adjusted to 7.0 with 0.1 mol/l NaOH); the BSA concentration is always equal to that during the "subsequent coating", and is thus respectively: x=1.6, 3.2, . . . , 51.2 g/l (see table).

The immuno-activity of the conjugates was ascertained by a DIA ("Sandwich test") in accordance with the procedure described in section 1.4. During this the following HCG dilution series was used: 0, 3.9, 15.6, 62.5, 250, 1,000, 4,000, 16,000 IU immunoassay/l.

| Conjugate HCG (IU/l) | $A_{516}$ | | | | | | | |
|---|---|---|---|---|---|---|---|---|
| | 0 | 3.9 | 15.6 | 62.5 | 250 | 1000 | 4000 | 16000 |
| 10.6-a | 0.322 | 0.397 | 0.378 | 0.436 | 0.565 | 0.773 | 0.954 | 1.034 |
| b | 0.254 | 0.282 | 0.286 | 0.344 | 0.489 | 0.707 | 0.892 | 0.960 |
| c | 0.137 | 0.154 | 0.175 | 0.235 | 0.397 | 0.661 | 0.812 | 0.906 |

-continued

| Conjugate HCG (IU/l) | $A_{516}$ | | | | | | | |
|---|---|---|---|---|---|---|---|---|
| | 0 | 3.9 | 15.6 | 62.5 | 250 | 1000 | 4000 | 16000 |
| d | 0.062 | 0.078 | 0.095 | 0.147 | 0.297 | 0.594 | 0.778 | 0.852 |
| e | 0.039 | 0.040 | 0.054 | 0.110 | 0.283 | 0.572 | 0.759 | 0.843 |
| f | 0.021 | 0.029 | 0.044 | 0.111 | 0.310 | 0.629 | 0.803 | 0.882 |

EXAMPLE 11

Colorimetric and/or visual determination of human chorionic gonadotropin (HCG) according to the DIA principle (aglutination test; method 1).

11.1. Preparation of the dye sol

See 1.1.

11.2. Preparation of the rabbit anti-HCG immunoglobulin/dye sol conjugate

See 1.2.; in this case however the BSA solution contains 2.4 g/l, because the pellet is resuspended in a solution having the described composition, but with 0.4 g BSA/l. The conjugate is finally further diluted up to a value of $A_{533}^{1 \, cm} = 2.2$.

11.3. Determination of HCG in phosphate buffer or urine TRIS buffer 1 mol TRIS+1 mol NaCl+10 g BSA/l, adjusted to pH 7.4 with 4 mol/l HCl.

HCG

See 1.4.

Urine

See 1.4.

Phosphate buffer (FFB)

See 1.4.

Conjugate

See 11.2.

Procedure

1. HCG solution of 5,000 and 1,000 IU (immunoassay)/l are made up by diluting the standard HCG solution with FFB or urine.

2. Pipette into a cell (1 cm light path): conjugate (1 ml), TRIS buffer (0.1 ml) and HCG solution (0.11 ml). Mix well and immediately scan the absorption spectrum in the region 750-360 nm, with FFB and urine respectively as reference.

3. Allow the cells to stand at room temperature for 20 hours. Then assess the contents by eye and shake the cells and then once again establish an absorption spectrum in the region 750-360 nm.

Representative spectra are given in FIG. 3, while numerical data are provided in the following table:

| HCG conc. (IU/l) | Visual* | $(A_{533})_o-(A_{533})_x$** | $(A_{575})_o-(A_{575})_x$ |
|---|---|---|---|
| 0 | − | 0 | 0 |
| 1000 | + | 0.15 | 0.14 |
| 5000 | ++ | 0.40 | 0.21 |

*"−": no agglutination/aggregation. Dye sol stable.
"+": incipient agglutination/aggregation. The supernatant is lighter in color than with the corresponding blank (O IU HCG/l) due to sedimentation.
"++": complete agglutination/aggregation. The dye sol has flocculated completely and the dye is precipitated.
**$o$: O IU HCG/l
$x$: 1 and 5 respectively, IU HCG/l.

EXAMPLE 12

Colorimetric determination of human chorionic gonadotropin (HCG) according to the DIA principle (agglutination test; method 2)

12.1. Preparation of dye sol.
See section 1.1.

12.2. General test procedure for DIA/agglutination

The dye-immunoglobulin conjugate (2 ml) was pipetted into a glass or polystyrene cuvette and mixed with 0.2 ml of the antigen sample dissolved in FFB (see section 1.4.), or 0.2 ml FFB only, and 0.2 ml of distilled water or of a solution of $MgSO_4$ in distilled water. The cuvettes were maintained at room temperature (without agitation) and the absorbances were determined (without prior agitation) after regular time intervals. The antigen causes agglutination of the dye sol particles, which yields a decrease in absorbance due to the increased effective particle size per se and due to the concomitant sedimentation of the aggregates.

All further experiments are concerned with the determination of HCG.

12.3. Preparation of the rabbit (anti HCG) IgG/dye conjugate

Standard procedure: see section 11.2

Optimalization was performed by investigating the following parameters:

12.3.1. Secondary coating of conjugates with BSA

Conjugates for DIA/sandwich are secondarily coated with BSA in order to reduce non-specific effects; this extra coating of the conjugate will certainly also improve its stability and will be disadvantageous therefore for conjugates to be used in DIA/agglutination. Conjugates coated with varying amounts of BSA, and also without BSA, were compared in the agglutination assay. The conjugate without BSA yielded the highest sensitivity and lowest detection limit in the shortest test period, and was still sufficiently stable to give a constant blank value.

12.3.2. Optimal IgG concentration during conjugate preparation

Palanil® Red BF/anti-HCG conjugates were prepared using different IgG concentrations during the coating, and were screened in the agglutination assay using a constant HCG concentration of 5 IU/ml sample (or: 0.42 IU/ml total test volume). The optimal IgG concentration during conjugate preparation appeared to be 0.033 mg/ml reaction mixture at a sol concentration corresponding with a $A_{530}^{1\ cm} = 5$.

12.3.3. Effect of incubation of IgG at pH 2.0 prior to conjugate preparation A solution of rabbit anti-HCG IgG (4-5 mg/ml in 5 mmol NaCl/l pH 7.0) was adjusted to pH 2.0 and incubated for 1 h. at 4° C.; the pH was readjusted to 7.4 and the IgG solution was used for conjugate preparation. The concentration of "pH 2 treated IgG" during the conjugate synthesis was varied, and the various conjugates were screened as described in 12.3.2.

A concentration of 0.033 mg "pH 2 treated IgG"/ml reaction mixture, at a sol concentration corresponding with $A_{530}^{1\ cm} = 5$, appeared to be the optimal value.

Comparison of conjugates based on native IgG and "pH 2 treated" IgG clearly demonstrated the advantage of the latter with respect to reactivity in the agglutination test:

| IgG in conjugate | (HCG) (IU/ml) | Decrease in $A_{530}^{1\ cm}$ (%) after 4 h. | after 18 h. |
|---|---|---|---|
| native IgG | 2.5 | 6 | 21 |
|  | 5 | 13 | 63 |
| pH-2 treated IgG | 2.5 | 14 | 74 |
|  | 5 | 28 | 100 |

12.3.4. Effect of additives on the reactivity of conjugates

Addition of a destabilizing agent (e.g. $MgSO_4$) to the conjugate prior to addition of the sample may yield a decrease in reaction time and/or detection limit of the agglutination assay, particularly in case of conjugates highly stable per se. Anti-HCG/Palanil® RED BF conjugates, based on the dye batches 5228513 (powder) and 4742893 (wet dispersion), were incubated with a dilution series of $MgSO_4$ yielding a final concentration range of 0–20 mmol $MgSO_4$/l total test mixture, and $A_{530}^{1\ cm}$ was determined at regular time intervals. Concentrations of 1.2 and 9.5 mmol $MgSO_4$/l total test mixture, respectively, were found to be compatible with a still suitable stability of the conjugates (decrease of $A_{530}^{1\ cm}$ less than 0.1–0.2 after 2 h).

A dilution series of HCG in FFB (see section 1.4.; 0–5 IU/ml sample) was incubated with anti-HCG/Palanil® Red BF (4742893) conjugate with and without 9.5 mmol $MgSO_4$/l total test mixture. The conjugate without $MgSO_4$ gave only a slight decrease in $A_{530}^{1\ cm}$, as compared to the blank, whereas in the presence of $MgSO_4$ a decrease in absorbance, significantly differing from the blank, was observed:

| [$MgSO_4$] (μmol/ml total test mixture) | (HCG) (IU/ml) | decrease in $A_{530}^{1\ cm}$ (%) (after 2.5 h) |
|---|---|---|
| 0 | 2.5 | 3 |
| 9.5 | 2.5 | 13 |
| 0 | 5.0 | 4 |
| 9.5 | 5.0 | 21 |

12.3.5. Reactivity of anti-HCG/Palanil® Red BF conjugate, based on "pH 2 treated" IgG, and in the presence of $MgSO_4$ The combined effects, described in 12.3.3./12.3.4. were investigated with Palanil® Red BF conjugates (based on the wet and dry commercial preparation), and a HCG dilution series in FFB (0–4 IU/ml sample). The obtained detection limits (defined as the concentration of HCG yielding a response equal to $(BL-2\times SD)$) are summarized below:

| Palanil® Red BF 5228513 (powder) | 120 IU/l (20 h) |
|---|---|
|  | 400 IU/l ( 4 h) |
| Palanil® Red BF 4742893 (dispersion) | 280 IU/l (20 h) |
|  | 1300 IU/l ( 4 h) |

The detection limit of SPIA/agglutination is 100 IU/l (colorimetric detection after 2 h).

12.3.6. Effect of particle size on conjugate reactivity

All experiments up to now were performed with only one fraction of the total dye dispersion, viz. the material remaining in the supernatant at 1,000–1,100 g (9,800–10,800 N/kg), which corresponds roughly with a particle size $\leq 0.2$ μm diameter. The effect of particle size was further investigated by preparing anti-HCG conjugates of different "g-fractions" of Palanil ® Red BF, and testing them in an HCG agglutination assay. Significant effects were observed (cf. FIGS. 4A and 4B), yielding optimal results for the dye fraction isolated between 1,500 and 2,500 g.

EXAMPLE 13

Lyophilization of disperse dye/immunoglobulin conjugates; stability.

A Palanil ® Red BF/rabbit anti-HCG conjugate was lyophilized from an aqueous dispersion ($A_{530}^{1 \ cm} \approx 5$) containing the following constituents:

| 5 mmol | NaCl | |
|---|---|---|
| 5 g | BSA | |
| 1 g | sodium merthiolate | per liter; |
| 2.5 g | dextran (Mw 40000 Dalton) | pH 7.0 |
| 5.0 g | lactose | |

The reconstituted dry conjugate showed no loss in reactivity as compared to the original wet preparation. The conjugate retains its immunoreactivity for at least 2½ months at −20° C., 4° C. and room temperature. Some loss in activity was found after 2½ months/37° C., a considerable loss was found after 2½ months/45° C.

We claim:

1. A process for the qualitative and/or quantitative determination of an immunochemically reactive component selected from the group consisting of a hapten, antigen, and antibody in an aqueous test medium using the immunochemical reactivity of said component comprising:
    (1) providing a known amount of at least one labelled immunochemically reactive component obtained by the direct or the indirect attachment of an immunochemically reactive component to particles of an aqueous dispersion of (a) a hydrophobic dye or pigment or (b) polymer nuclei coated with said dye or pigment, said particles having a particle size of at least 5 nm;
    (2) providing at least one non-labelled immunochemically reactive component;
    (3) mixing said components (1) and (2) with a sample containing said test medium;
    (4) allowing the immunochemical reaction to proceed to form free and bound labelled component(s);
    (5) optionally separating the free and bound labelled component(s) in the test medium or in one of the fractions obtained after separation; and
    (6) determining the nature and/or the quantity of the dye or pigment, said determination providing a qualitative and/or quantitative indication of the immunochemically reactive component(s) to be determined.

2. The process of claim 1, wherein the determination (6) takes place by the detection and determination of the physicochemical changes of a dye sol.

3. The process of claim 1 or claim 2, wherein two or more immunochemically reactive components are determined simultaneously, wherein for each component to be determined there is present a corresponding immunochemically reactive component that is labelled with a dye sol particle respective for that component, and further wherein respective chromophores are used that can clearly be distinguished from each other spectrally and/or visually.

4. The process of claim 1, further comprising obtaining the labelled component by adding to the dye or pigment dispersion a predetermined quantity of the immunochemically reactive component to be labelled, wherein the latter at least partially envelopes the dispersed particles and optionally supplementary coating said particles with a polar macromolecule that is immunochemically inert in the corresponding determination.

5. The process of claim 1, wherein the labelled component is obtained by adding to said dispersion of dye or pigment at least one macromolecule that is immunochemically inert in the corresponding determination and that coats the dispersion particles and thereafter attaching by adsorption, possibly bio-specific, or via covalent attachment the immunochemically reactive component to the coating material.

6. The process of claim 1, wherein the labelled component is obtained by placing a dye and/or organic pigment sol in a monomer environment and causing the latter to be polymerised in situ, resulting in envelopment of the sol particles, and subsequently absorbing or covalently attaching the immunochemically reactive component to the polymer material.

7. The process of claim 1, wherein the labelled component is obtained by covalently attaching the immunochemically reactive component to colloidal dye particles, either by prior chemical activation of suitable functional groups in the dye and/or the immunochemically reactive component, or by the use of conjugates of organic hydrophobic chromophores and reactive groups, known as reactive (dispersion) dyes.

8. The process of claim 5 wherein the dye and/or organic pigment sol particles are first protected by a hydrophilic macromolecule after which (co-)polymerisation takes place in the presence of an organic initiator.

9. A test kit for the determination of one or more immunochemically reactive components in an aqueous medium, comprising:
    (a) a known amount of at least one labelled immunochemically reactive component obtained by the direct or indirect attachment of an unlabelled immunochemically reactive component to particles of an aqueous dispersion of (i) a hydrophobic dye or pigment or (ii) polymer nucleic coated with said dye or pigment, said particles having a particle size of at least 5 nm,
    (b) other immunochemical reagents, and
    (c) directions for use of said test kit.

10. An immunochemical reagent consisting of an aqueous dispersion of particles of (a) a hydrophobic dye or pigment or (b) polymer nuclei coated with said dye or pigment directly or indirectly attached to an immunochemically reactive component, said particles having a particle size of at least 5 nm.

11. A freeze-dried or spray dried reagent containing at least one labelled immunochemically reactive component obtained by direct or indirect attachment of an unlabelled immunochemically reactive component to particles of an aqueous dispersion of (a) a hydrophobic dye or pigment or (b) polymer nuclei coated with said dye or pigment, said labelled immunochemically reactive component being freeze-dried or spray dried and said particles having a particle size of at least 5 nm.

12. A process for the detection and/or determination of at least one immunochemically reactive component in an aqueous test medium comprising:
    providing a known amount of at least one labelled immunochemically reactive component having attached thereto particles of an aqueous dispersion of (a) a hydrophobic dye or pigment or (b) polymer nuclei coated with a hydrophobic dye or pigment, said particles having a particle size of at least 5 nm;

providing an aqueous test medium containing at least one immunochemically reactive component to be detected or determined;

contacting said labelled immunochemically reactive component(s) with said immunochemically reactive component(s) to be detected or determined; and measuring the presence or quantity of said hydrophobic dye or pigment to provide a measure of the immunochemically reactive component(s) to be detected or determined.

13. The process of claim 12 wherein the immunochemically reactive components are selected from the group consisting of an antigen, an antibody, and a hapten.

14. The process of claim 12 wherein said aqueous dispersion of a hydrophobic dye or pigment is a sol.

15. The process of claim 14 wherein said hydrophobic dye or pigment has a particle size of about 10 to about 500 nm.

16. An immunochemical reagent comprising an immunochemically reactive component having coupled thereto a member selected from the group consisting of particles of (a) a hydrophobic dye or pigment or (b) polymer nuclei coated with a hydrophobic dye or pigment, said particles having a particle size of at least 5 nm.

17. The immunochemical reagent of claim 16 which is freeze-dried.

18. The immunochemical reagent of claim 16 which is spray-dried.

19. The immunochemical reagent of claim 16 wherein said particles of a hydrophobic dye or pigment are provided by an aqueous dispersion of said particles.

20. The immunochemical reagent of claim 19 wherein said aqueous dispersion is a sol.

21. The immunochemical reagent of claim 20 wherein said particles have a size of about 10 to about 500 nm.

22. A test kit for the determination of at least one immunochemically reactive component in an aqueous medium, comprising:
(a) a known amount of at least one immunochemical reagent comprising an immunochemically reactive component having coupled thereto a member selected from the group consisting of particles of a hydrophobic dye or pigment and polymer nuclei coated with a hydrophobic dye or pigment, said particles having a particle size of at least 5 nm,
(b) other immunochemical reagents; and
(c) directions for use of said test kit.

23. A process for the detection and/or determination of at least one component of the reaction between a specific binding protein and the corresponding bindable substance in an aqueous test sample, by applying the known binding affinity of such said protein and said substance for one another, comprising:
(a) mixing a known amount of one or more labelled components, obtained by coupling directly or indirectly the desired component of said reaction with particles of an aqueous dispersion of a hydrophobic dye or pigment or polymer nuclei coated with a hydrophobic dye or pigment, said particles having a particle size of at least 5 nm, and
(b) detecting and/or determining during the reaction or after an adequate reaction time and optionally after separation of the bound and free labelled components, the physical properties and/or the amount of said dye or pigment and/or a formed agglomerate containing said dispersed particles in the test sample or one of the derived fractions, which detection and/or determination provides a qualitative and/or quantitative indication of the component or components to be detected and/or determined.

24. The process of claim 23, whereby the component or components of the reaction between a specific binding protein and the corresponding bindable substances are immunochemical components selected from the group consisting of haptens, antigens, and antibodies, comprising:
(a) employing a known amount of labelled components, obtained by coupling directly or indirectly the desired immunochemical component to particles of an aqueous dispersion of (i) a hydrophobic dye or pigment or (ii) polymer nuclei coated with a hydrophobic dye or pigment, said particles having a particle size of at least 5 nm, and
(b) detecting or determining after an adequate reaction time and optionally after separation of the bound and free labelled components, the physical properties and/or the amount of said dye or pigment and/or a formed agglomerate containing said dye or pigment particles in the test sample or one of the derived fractions, which detection and/or determination provides a qualitative and/or quantitative indication of the immunochemical component or components to be detected and/or determined.

25. A test kit, to be used for the determination of one or more components of the reaction between a specific binding protein and the corresponding bindable substance in an aqueous medium according to a predetermined protocol, comprising:
(a) a known amount of a hydrophobic dye or pigment-labelled component that has been obtained by coupling a component of said reaction to particles of an aqueous dispersion of a hydrophobic dye or pigment or polymer nuclei coated with a hydrophobic dye or pigment, said particles having a particle size of at least 5 nm;
(b) other immunochemical reagents; and
(c) directions for the performance of said protocol.

26. A freeze-dried reagent for use in an immunoassay, containing a hydrophobic dye or pigment-labelled component, that has been obtained by coupling directly or indirectly the desired component to particles of an aqueous dispersion of a hydrophobic dye or pigment or polymer nuclei coated with a hydrophobic dye or pigment, said particles having a particle size of at least 5 nm.

27. A method for the determination of a first component of an immunochemical reaction in an aqueous medium selected from the group consisting of a specific binding protein and its corresponding bindable substance, comprising:
(a) contacting a sample containing the first component to be determined with (1) a known amount of a reagent consisting essentially of hydrophobic dye or pigment dispersion particles having a particle size of at least 5 nm, which particles have attached to their surfaces an immunochemical component which is at least immunochemically equivalent to said first component to be determined, and (2) a known amount of an insolubilized second component capable of reacting with either said first component to be determined or said reagent;
(b) allowing sufficient time for reaction to take place, whereby (1) a fraction of said first component to be determined bound to said insolubilized component, and (2) a fraction of said first component to be determined free from said insolubilized component are produced; and
(c) determining the amount of the dye or pigment of the dispersion particles in one of said fractions, which is a measure of the amount of said first component to be determined in said sample.

28. A method for the determination of a first component of an immunochemical reaction in an aqueous medium, selected from the group consisting of a specific binding protein and its corresponding bindable substance, comprising:
(a) contacting a sample containing the first component to be determined with (1) a known amount of a reagent consisting essentially of hydrophobic dye or pigment dispersion particles having a particle size of at least 5 nm, which particles have attached to their surfaces (i) an immunochemical component which is at least immunochemically equivalent to said first component to be determined and (ii) an immunochemically inert macromolecule, and (2) a known amount of an insolubilized second immunochemical component capable of reacting with either said first component to be determined or said reagent;
(b) allowing sufficient time for reaction to take place, whereby (1) a fraction of said first component to be determined bound to said insolubilized component and (2) a fraction of said first component to be determined free from said insolubilized component are produced; and
(c) determining the amount of the dye or pigment of the dispersion particles in one of said fractions, which is a measure of the amount of said first component to be determined in said sample.

29. A method for the determination of a first component of an immunochemical reaction in an aqueous medium, selected from the group consisting of a specific binding protein and its corresponding bindable substance, comprising:
(a) contacting a sample containing the first component to be determined with (1) a known amount of a reagent consisting essentially of hydrophobic dye or pigment dispersion particles having a particle size of at least 5 nm, which particles have a coating of an inert hydrophilic polymer or copolymer, the surface of each coated particle having attached to it an immunochemical component which is at least immunochemically equivalent to said first component, and (2) a known amount of an insolubilized second immunochemical component capable of reacting with either said first component to be determined or said reagent;
(b) allowing sufficient time for reaction to take place, whereby (1) a fraction of said first component to be determined bound to said insolubilized component and (2) a fraction of said first component to be determined free from said insolubilized component are produced; and
(c) determining the amount of the dye or pigment of the dispersion particles in one of said fractions, which is a measure of the amount of said first component to be determined in said sample.

30. A method for the determination of a first component of an immunochemical reaction in an aqueous medium, selected from the group consisting of a specific binding protein and its corresponding bindable substance, comprising:
(a) contacting a sample containing the first component to be determined with (1) a known amount of a reagent consisting essentially of hydrophobic dye or pigment dispersion particles having a particle size of at least 5 nm, which particles have attached to their surfaces a second immunochemical component of said reaction capable of reacting with said first component to be determined, and (2) a known amount of an insolubilized second immunochemical component which is at least immunochemically equivalent to said first component and capable of reacting with said reagent;
(b) allowing sufficient time for reaction to take place, whereby (1) a fraction of said first component to be determined bound to said insolubilized component and (2) a fraction of said first component to be determined free from said insolubilized component are produced; and
(e) determining the amount of the dye or pigment of the dispersion particles in one of said fractions, which is a measure of the amount of said first component to be determined in said sample.

31. A method for the determination of a first component of an immunochemical reaction in an aqueous medium, selected from the group consisting of a specific binding protein and its corresponding bindable substance, comprising:
(a) contacting a sample containing the first component to be determined with (1) a known amount of a reagent, said reagent consisting essentially of hydrophobic dye or pigment dispersion particles having a particle size of at least 5 nm, which particles have attached to their surfaces (i) a second immunochemical component capable of reacting with said first component to be determined and (ii) an immunochemically inert macromolecule, and (2) a known amount of an insolubilized second immunochemical component which is at least immunochemically equivalent to said first component to be determined and capable of reacting with said reagent;
(b) allowing sufficient time for the reaction to take place, whereby (1) a fraction of said first component to be determined bound to said insolubilized component and (2) a fraction of said first component to be determined free from said insolubilized component are produced; and
(c) determining the amount of the dye or pigment of the dispersion particles in one of said fractions, which is a measure of the amount of said first component to be determined in said sample.

32. A method for the determination of a first component of an immunochemical reaction in an aqueous medium, selected from the group consisting of a specific binding protein and its corresponding bindable substance, comprising:
(a) containing a sample containing the first component to be determined with (1) a known amount of a reagent consisting essentially of hydrophobic dye or pigment dispersion particles having a particle size of at least 5 nm, which particles have a coating of an inert hydrophilic polymer of copolymer, the surface of each coated particle having attached to it a second immunochemical component of said reaction capable of reacting with said first component to be determined, and (2) a known amount of an insolubilized third immunochemical component and capable of reacting with said reagent;

(b) allowing sufficient time for the reaction to take place, whereby a fraction of said first component to be determined bound to said insolubilized component and a fraction of said first component to be determined free from said insolubilized component are produced; and (c) determining the amount of the dye or pigment of the dispersion particles in one of said fractions, which is a measure of the amount of said first component to be determined in said sample.

33. A method for the determination of a first component of an immunochemical reaction in an aqueous medium, selected from the group consisting of a specific binding protein and its corresponding bindable substance, comprising:

(a) binding a known amount of a second immunochemical component of said reaction capable of reacting with said first component to be determined, to the surface of a water-insoluble, water-insuspensible, solid carrier;

(b) contacting said bound second component with a sample containing the first component to be determined;

(c) allowing sufficient time for reaction to take place;

(d) contacting said bound reaction product of (c) with a known amount of a reagent consisting essentially of hydrophobic dye or pigment dispersion particles having a particle size of at least 5 nm, which particles have attached to their surface an immunochemical component capable of reacting with said first component to be determined;

(e) allowing sufficient time for reaction to take place, to bind a fraction of said reagent to that part of said bound second immunochemical component which has undergone the reaction step (c), leaving a remaining fraction of said reagent free and not bound; and (f) determining the amount of the dispersion particles in the free reagent fraction or the bound reagent fraction, which is a measure of the amount of said first component to be determined in said sample.

34. A method for the determination of a first component of an immunochemical reaction in an aqueous medium, selected from the group consisting of a specific binding protein and its corresponding bindable substance, comprising:

(a) binding a known amount of a second immunochemical component capable of reacting with said first component to be determined, to the surface of a water-insoluble, water-insuspensible, solid carrier;

(b) contacting said bound second component with a sample containing the first component to be determined;

(c) allowing sufficient time for reaction to take place;

(d) contacting said bound reaction product of step (c) with an immunochemical excess of a reagent consisting essentially of hydrophobic dye or pigment dispersion particles having a particle size of at least 5 nm, said particles having attached to their surfaces (i) an immunochemical component capable of reacting with said first component to be determined and (ii) an immunochemically inert macromolecule;

(e) allowing sufficient time for reaction to take place to bind a fraction of said reagent to that part of said bound second component which has undergone the reaction in step (c), leaving a remaining fraction of said reagent free and not bound; and (f) determining the amount of the dye or pigment dispersion particles in the free reagent fraction or the bound reagent fraction, which is a measure of the amount of said component to be determined in said sample.

35. A method for the determination of a first component of an immunochemical reaction in an aqueous medium, selected from the group consisting of a specific binding protein and its corresponding bindable substance, comprising:

(a) binding a known amount of a second immunochemical component capble of reacting with said first component to be determined, to the surface of a water-insoluble, water-insuspensible, solid carrier;

(b) contacting said bound second component with a sample containing the first component to be determined;

(c) allowing sufficient time for reaction to take place;

(d) contacting said bound reaction product of step (c) with an immunochemical excess of a reagent consisting essentially of hydrophobic dye or pigment dispersion particles having a particle size of at least 5 nm and having a coating of an inert hydrophilic polymer or copolymer, the surface of each coated particle having attached to it an immunochemical component capable of reacting with said first component to be determined;

(e) allowing sufficient time for reaction to take place to bind a fraction of said reagent to that part of said bound second component which has undergone the reaction in step (c), leaving a remaining fraction of said reagent free and not bound; and (f) determining the amount of the dye or pigment dispersion particles in the free reagent fraction or the bound reagent fraction, which is a measure of the amount of said first component to be determined in said sample.

36. A method for the determination of a first component of an immunochemical reaction in an aqueous medium, selected from the group consisting of a specific binding protein and its corresponding bindable substances, comprising:

(a) contacting a sample containing the first component to be determined with a known amount of a reagent, said reagent consisting essentially of hydrophobic dye or pigment dispersion particles having a particle size of at least 5 nm, said particles having attached to their surfaces a second immunochemical component of said reaction capable of reacting with said first component to be determined;

(b) allowing sufficient time for reaction to take place; and (c) determining the color of the reaction solution, which is a measure of the amount of said first component to be determined in said sample.

37. A method for the determination of a first component of an immunochemical reaction in an aqueous medium, selected from the group consisting of a specific binding protein and its corresponding bindable substance, comprising:
 (a) contacting a sample containing the first component to be determined with a known amount of a reagent consisting essentially of hydrophobic dye or pigment dispersion particles having a particle size of at least 5 nm, said particles having attached to their surfaces (i) a second immunochemical component of said reaction capable of reacting with said first component to be determined and (ii) an immunochemically inert macromolecule;
 (b) allowing sufficient time for a reaction to take place; and
 (c) determining the color of the reaction solution, which is a measure of the amount of said first component to be determined in said sample.

38. A method for the determination of a first component of an immunochemical reaction in an aqueous test medium selected from the group consisting of a specific binding protein and its corresponding bindable substance, comprising:
 (a) contacting a sample containing the first component to be determined with a known amount of a reagent consisting of hydrophobic dye or pigment dispersion particles having a particle size of at least 5 nm, said particles having a coating of an inert hydrophilic polymer or copolymer, the surface of each coated particle having attached to it a second immunochemical component of said reaction capable of reacting with said first component to be determined;
 (b) allowing sufficient time for a reaction to take place; and
 (c) determining the color of the reaction solution, which is a measure of the amount of said first component to be determined in said sample.

39. A method for the immunochemical determination of human chorionic gonadotropin (HCG), comprising:
 (a) binding a known amount of rabbit anti-HCG immunoglobulin to the surface of a water-insoluble, water-insuspensible solid carrier;
 (b) contacting said bound immunoglobulin with a sample solution containing the HCG to be determined;
 (c) allowing sufficient time for an immunological reaction between the bound immunoglobulin and said HCG in the sample soution in step (b) to take place, to bind the HCG to be determined to the insolubilized rabbit anti-HCG, forming a first solid phase and leaving a first liquid phase;
 (d) separating the first liquid and solid phases;
 (e) contacting said first reacted solid phase and bound HCG therein with an immunochemical excess of a reagent, said reagent consisting essentially of Palanil Red BF dispersion particles having a particle size of at least 5 nm, said particles having rabbit anti-HCG immunoglobulin attached to their surfaces;
 (f) allowing sufficient time for a second immunological reaction to take place, to bind said reagent to that part of said HCG solid phase bound immunoglobulin which has undergone the reaction in step (c), to form a second solid phase and a second liquid phase;
 (g) separating the second solid phase from the second liquid phase; and
 (h) determining the amount of Palanil Red BF in the second liquid phase or the second solid phase, which is a measure of the amount of HCG in said sample solution.

40. A method for the immunochemical determination of human chorionic gonadotropin (HCG), comprising:
 (a) binding a known amount of rabbit anti-HCG immunoglobulin to the surface of a water-insoluble, water-insuspensible solid carrier;
 (b) contacting said bound immunoglobulin with a sample solution containing the HCG to be determined;
 (c) allowing sufficient time for an immunological reaction between the bound immunoglobulin and said HCG in the sample solution in step (b) to take place, to bind the HCG to be determined to the insolubilized rabbit anti-HCG, forming a first solid phase and leaving a a first liquid phase;
 (d) separating the first liquid and solid phases;
 (e) contacting said first reacted solid phase and bound HCG therein with an immunochemical excess of a reagent, said reagent consisting essentially of Resolin Brilliant Blue RRL dispersion particles having a particle size of at least 5 nm, said particles having rabbit anti-HCG immunoglobulin attached to their surfaces;
 (f) allowing sufficient time for a second immunological reaction to take place, to bind said reagent to that part of said HCG solid phase bound immunoglobulin which has undergone the reaction in step (c), to form a second solid phase and a second liquid phase;
 (g) separating the second solid phase from the second liquid phase; and
 (h) determining the amount of Resolin Brilliant Blue RRL in the second liquid phase or the second solid phase, which is a measure of the amount of HCG in said sample solution.

41. A method for the immunochemical determination of human chorionic gonadotropin (HCG), comprising:
 (a) binding a known amount of rabbit anti-HCG immunoglobulin to the surface of a water-insoluble, water-insuspensible solid carrier;
 (b) contacting said bound immunoglobulin with a sample solution containing the HCG to be determined;
 (c) allowing sufficient time for an immunological reaction between the bound immunoglobulin and said HCG in the sample solution in step (b) to take place, to bind the HCG to be determined to the insolubilized rabbit anti-HCG, forming a first solid phase and leaving a first liquid phase;
 (d) separating the first liquid and solid phases;
 (e) contacting said first reacted solid phase and bound HCG therein with an immunochemical excess of a reagent, said reagent consisting essentially of Samaron Brilliant Red H6GF dispersion particles having a particle size of at least 5 nm, said particles having rabbit anti-HCG immunoglobulin attached to their surfaces;
 (f) allowing sufficient time for a second immunological reaction to take place, to bind said reagent to that part of said HCG solid phase bound immunoglobulin which has undergone the reaction in step (c), to form a second solid phase and a second liquid phase;
 (g) separting the second solid phase from the second liquid phase; and
 (h) determining the amount of Samaron Brilliant Red H6GF in the second liquid phase or the second solid phase, which is a measure of the amount of HCG in said sample solution.

42. A method for the immunochemical determination of human chorionic gonadotropin (HCG), comprising:
(a) binding a known amount of rabbit anti-HCG immunoglobulin to the surface of a water-insoluble, water-insuspensible solid carrier;
(b) contacting said bound immunoglobulin with a sample solution containing the HCG to be determined;
(c) allowing sufficient time for an immunological reaction between the bound immunoglobulin and said HCG in the sample solution in step (b) to take place, to bind the HCG to be determined to the insolubilized rabbit anti-HCG, forming a first solid phase and leaving a first liquid phase;
(d) separating the first and solid phases;
(e) contacting said first reacted solid phase and bound HCG therein with an immunochemical excess of a reagent, said reagent consisting essentially of Samaron Brilliant Yellow HIOGF dispersion particles having a particle size of at least 5 nm, said particles having rabbit anti-HCG immunoglobulin attached to their surfaces;
(f) allowing sufficient time for a second immunological reaction to take place, to bind said reagent to that part of said HCG solid phase bound immunoglobulin which has undergone the reaction in step (c), to form a second solid phase and a second liquid phase;
(g) separating the second solid phase from the second liquid phase; and
(h) determining the amount of Samaron Brilliant Yellow HIOGF in the second liquid phase or the second solid phase, which is a measure of the amount of HCG in said sample solution.

43. A method for the immunochemical determination of human chorionic gonadotropin (HCG), comprising:
(a) binding a known amount of rabbit anti-HCG immunoglobulin to the surface of a water-insoluble, water-insuspensible solid carrier;
(b) contacting said bound immunoglobulin with a sample solution containing the HCG to be determined;
(c) allowing sufficient time for an immunological reaction between the bound immunoglobulin and said HCG in the sample solution in step (b) to take place, to bind the HCG to be determined to the insolubilized rabbit anti-HCG, forming a first solid phase and leaving a first liquid phase;
(d) separating the first liquid and solid phases;
(e) contacting said first reacted solid phase and bound HCG therein with an immunochemical excess of a reagent, said reagent consisting essentially Palanil Luminous Red G dispersion particles having a particle size of at least 5 nm, said particles having rabbit anti-HCG immunoglobulin attached to their surfaces;
(f) allowing sufficient time for a second immunological reaction to take place, to bind said reagent to that part of said HCG solid phase bound immunoglobulin which has undergone the reaction in step (c), to form a second solid phase and a second liquid phase;
(g) separating the second solid phase from the second liquid phase; and
(h) determining the amount of Palanil Luminous Red G in the second liquid phase or the second solid phase, which is a measure of the amount of HCG in said sample solution.

44. A method for the immunochemical determination of human chorionic gonadotropin (HCG), comprising:
(a) binding a known amount of rabbit anti-HCG immunoglobulin to the surface of a water-insoluble, water-insuspensible solid carrier;
(b) contacting said bound immunoglobulin with a sample solution containing the HCG to be determined;
(c) allowing sufficient time for an immunological reaction between the bound immunoglobulin and said HCG in the sample solution in step (b) to take place, to bind the HCG to be determined to the insolubilized rabbit anti-HCG, forming a first solid phase and leaving a first liquid phase;
(d) separating the first liquid and solid phases;
(e) contacting said first reacted solid phase and bound HCG therein with an immunochemical excess of a reagent, said reagent consisting essentially of Palanil Luminous Yellow G dispersion particles having a particle size of at least 5 nm, said particles having rabbit anti-HCG immunoglobulin attached to their surfaces;
(f) allowing sufficient time for a second immunological reaction to take place, to bind said reagent to that part of said HCG to said phase bound immunoglobulin which has undergone the reaction in step (c), to form a second solid phase and a second liquid phase;
(g) separating the second solid phase from the second liquid phase; and
(h) determining the amount of Palanil Luminous Yellow G in the second liquid phase or the second solid phase, which is a measure of the amount of HCG in said sample solution.

45. A method for the immunochemical determination of hepatitis Surface B antigen (HBsAg), comprising:
(a) binding a known amount of sheep anti-HBsAg immunoglobulin to the surface of a water-insoluble, water-insuspensible solid carrier;
(b) contacting said bound immunoglobulin with a sample solution containing the HBsAg to be determined;
(c) allowing sufficient time for an immunological rection between the bound immunoglobulin and the HBsAg in the sample solution in step (b) to take place, to bind the HBsAg to be determined to the insolubilized sheep anti-HBsAg, forming a first solid phase and leaving a first liquid phase;
(d) separating the first liquid and solid phases;
(e) contacting said first reacted solid phase and bound HBsAg therein with an immunochemical excess of particles of Palanil Red BF or Samuron Brilliant Red H6GF particles having anti-HBsAg immunoglobulin attached to their surfaces, said particles having a particle size of at least 5 nm;
(f) allowing sufficient time for a second immunochemical reaction to take place, to bind said reagent to that part of said HBsAg solid phase bound immunoglobulin which has undergone the reaction in step (c), to form a second solid phase and a second liquid phase;
(g) separating the second solid phase from the second liquid phase; and
(h) determining the amount of Palanil Red BF or Samuron Brilliant Red H6GF in the second liquid phase or the second solid phase, which is a measure of the amount of HBsAg in said sample solution.

46. A method for the immunochemical determination of human placental lactogen (HPL) in a liquid sample, comprising:
   (a) binding a known amount of rabbit anti-HPL immunoglobulin to the surface of a water-insoluble, water-insuspensible, solid carrier;
   (b) contacting said bound rabbit anti-HPL with a sample solution containing the HPL to be determined;
   (c) allowing sufficient time for an immunological reaction between the bound rabbit anti-HPL immunoglobulin and the HPL in the sample solution in step (b) to take place to bind the HPL to be determined to the insolubilized rabbit anti-HPL, forming a first solid phase and leaving a first liquid phase;
   (d) separating the first liquid and solid phases;
   (e) contacting said first reacted solid phase and bound HPL therein with a known amount of particles of a Palanil Red BF or Palanil Yellow 36 to form a particle-HPL conjugate, said particles having a particle size of at least 5 nm;
   (f) allowing sufficient time for a second immunochemical reaction to take place to bind said reagent to that part of said solid phase bound rabbit anti-HPL immunoglobulin which has not undergone the reaction in step (c), to form a second solid phase and a second liquid phase;
   (g) separating the second solid phase from the second liquid phase; and
   (h) determining the amount of Palanil Red BF or Palanil Yellow 36 in the second solid phase or the second liquid phase, which is a measure of the amount of testosterone in said liquid sample.

47. A method for the immunochemical determination of human anti-Rubella sera, comprising:
   (a) binding a known amount of Rubella viral antigen to the surface of a water-insoluble, water-insuspensible, solid carrier;
   (b) contacting said bound Rubella viral antigen with a human serum sample containing the human anti-Rubella sera to be determined;
   (c) allowing sufficient time for an immunological reaction between the bound Rubella viral antigen and the serum containing the human anti-Rubella sera to be determined to take place to bind the anti-Rubella sera to the insolubilized Rubella viral antigen, forming a first solid phase and leaving a first liquid phase;
   (d) separating the first liquid and solid phases;
   (e) contacting said first reacted solid phase and bound anti-Rubella titer therein with a known amount of a reagent consisting essentially of dispersion particles of Palanil Red BF or Resolin Brilliant Blue RRL, said particles having a particle size of at least 5 nm and having sheep anti-human immunoglobulin attached to their surfaces to form a particle-sheep anti-human immunoglobulin conjugate;
   (f) allowing sufficient time for a second immunological reaction to take place to bind said reagent to the bound anti-Rubella titer solid phase, resulting in the binding of said reagent to that part of said bound antigen which has undergone the reaction in step (c), to form a second solid and a second liquid phase;
   (g) separating the second liquid and solid phases; and
   (h) determining the amount of Palanil Red BF or Resolin Brilliant Blue RRL in the second solid phase or the second liquid phase, which is a measure of the human anti-Rubella serum to be determined in said sample.

48. A method for the immunochemical determination of human prolactin (PRL), comprising:
   (a) binding a known amount of monoclonal (anti-PRL) immunoglobulin to the surface of a water-insoluble, water-insuspensible solid carrier;
   (b) contacting said bound monoclonal (anti-PRL) immunoglobulin with a sample solution containing the PRL to be determined;
   (c) allowing sufficient time for an immunological reaction between the monoclonal (anti-PRL) immunoglobulin and the PRL in the sample solution in step (b) to take place, to bind the PRL to be determined to the insolubilized monoclonal (anti-PRL) immunoglobulin, forming a first solid phase and leaving a first liquid phase;
   (d) separating the first solid phase from the first liquid phase;
   (e) contacting said first solid phase and bound PRL with a known amount of a reagent consisting essentially of dispersion particles of Palanil Luminous Red G or Palanil Luminous Yellow G, said particles having a particles size of at least 5 nm and having monoclonal (anti-PRL) immuno-globulin attached to their surfaces;
   (f) allowing sufficient time for a second immunological reaction to occur to bind said reagent to that part of said PRL solid phase bound immuno-globuliln which has undergone the reaction in step (c), to form a second solid phase and a second liquid phase;
   (g) separating the second solid and second liquid phases; and
   (h) determining the amount of Palanil Luminous Red G or Palanil Luminous Yellow G in the second solid phase or the second liquid phase, which is a measure of the amount of the PRL to be determined in said sample solution.

49. A method for the immunochemical determination of human chorionic gonadtropin (HCG), comprising:
   (a) contacting an aqueous sample containing the HCG to be determined with a known amount of a reagent consisting essentially of dispersion particles of a hydrophobic dye or pigment, said particles having a particle size of at least 5 nm and having rabbit anti-HCG immunoglobulin attached to their surfaces;
   (b) allowing sufficient time for an immunological reaction between said reagent and any HCG in the sample solution to take place; and
   (c) determining the color of the sample solution, which is a measure of the amount of HCG to be determined in said sample solution.

50. The method of claim 44 wherein said hydrophobic dye or pigment is Palanil Red FF.

51. A method for the simultaneous determination of human chorionic gonadotropin (HCG) and human placental lactogen (HPL), comprising:
   (a) binding a known amount of rabbit anti-HCG immunoglobulin and a known amount of rabbit anti-HPL immunoglobulin to the surface of a water-insoluble, water-insuspensible solid carrier;

(b) contacting said bound immunoglobulins with a sample containing the HCG and the HPL to be determined;
(c) allowing sufficient time for an immunological reaction between the bound immunoglobulins and said HCG and said HPL in the sample solution in step (b) to take place, to bind the HCG to be determined to the insolubilized rabbit anti-HCG and to bind the HPL to be determined to the insolubilized rabbit anti-HPL, forming a first solid phase and leaving a first liquid phase;
(d) separating the first liquid and solid phases;
(e) contacting said first reacted solid phase and bound HCG therein with a known amount of a reagent, said reagent consisting essentially of Resolin Brilliant Blue RRL dispersion particles having a particle size of at least 5 nm, said particles having rabbit anti-HCG immunoglobulin attached to their surfaces;
(f) contacting said first reacted solid phase and bound HPL therein with a known amount of a reagent, said reagent consisting essentially of Palanil Yellow 36 dispersion particles, said particles having rabbit anti-HPL immunoglobulin attached to their surfaces;
(g) allowing sufficient time for a second immunological reaction to take place, to bind the reagent containing Resolin Brilliant Blue RRL dispersion particles to that part of said HCG solid phase bound immunoglobulin which has undergone the reaction in step (c) and to bind the reagent containing Palanil Yellow 36 dispersion particles to that part of said HPL solid phase bound immunoglobulin which has undergone the reaction in step (c);
(h) separating the second solid phase from the second liquid phase; and
(i) determining the presence of Resolin Brilliant Blue RRL and Palanil Yellow 36 in the second liquid phase or the second solid phase, which is an indicator or HCG and HPL respectively in the sample solution.

52. A method for the immunological determination of testosterone in a liquid sample, comprising:
(a) binding a known amount of rabbit anti-testosterone immunoglobulin to the surface of a water-insoluble, water-insuspensible solid carrier;
(b) contacting said bound rabbit anti-testosterone with a sample solution containing the testosterone to be determined;
(c) allowing sufficient time for an immunological reaction between the bound rabbit anti-testosterone immunoglobulin and the testosterone in the sample solution in step (b) to take place to bind the testosterone to be determined to the insolubilized rabbit anti-testosterone, forming a first solid phase and leaving a first liquid phase;
(d) separating the first liquid and solid phases;
(e) contacting said first reacted solid phase and bound testosterone therein with a known amount of particles of Palanil Red BF, said particles having a particle size of at least 5 nm and having testosterone 11 α-hemisuccinyl bovine serum albumin attached to their surfaces to form a particle-testosterone-11 α-hemisuccinyl bovine serum albumin conjugate;
(f) allowing sufficient time for a second immunological reaction to take place to bind said reagent to that part of said solid phase rabbit anti-testosterone immunoglobulin which has not undergone the reaction in step (c), to form a second solid phase and a second liquid phase;
(g) separating the second solid phase from the second liquid phase; and
(h) determining the amount of Pananil Red BF in the second solid phase, which is a measure of the amount of testosterone in said liquid sample.

53. A method for the immunological determination of testosterone in a liquid sample, comprising:
(a) contacting an aqueous sample containing the testosterone to be determined with (1) a known amount of a reagent consisting essentially of Samaron Brilliant Red H6GF or Samaron Brilliant Yellow H10GF particles, the particles having a particle size of at least 5 nm and having attached thereto rabbit anti-$T^{11}$-bovine serum albumin immunoglobulin and (2) a known amount of $T^3$-bovine serum albumin;
(b) allowing sufficient time for a reaction to take place, whereby a first fraction of testosterone bound to said $T^3$-bovine serum albumin and a fraction of testosterone free of $T^3$-bovine serum albumin are produced; and
(c) determining the amount of Samaron Brilliant Red H6GF or Samaron Brilliant Yellow H10GF particles in one of said fractions, which is a measure of the amount of testosterone in said sample.

54. A method for the determination of human chorionic gonadtropin (HCG), comprising:
(a) binding a known amount of HCG receptor protein to the surface of a water-insoluble, water-insuspensible solid carrier;
(b) contacting said bound receptor protein with a sample solution containing the HCG to be determined;
(c) allowing sufficient time for an immunological reaction between the insolubilized HCG receptor protein and the HCG to be determined;
(d) adding a known amount of reagent to said sample solution, said reagent consisting essentially of dispersion particles of a hydrophobic dye or pigment and having HCG attached to their surfaces, said particles having a particle size of at least 5 nm;
(e) allowing sufficient time for a reaction to take place between (1) the dispersion reagent and (2) the insolubilized HCG receptor protein not bound to HCG, to form a solid phase containing a fraction of dispersion reagent bound to insolubilized HCG receptor protein, and a liquid phase of unbound and free dispersion reagent;
(f) separating the liquid and solid phases; and
(g) determining the amount of dye or pigment in either the solid or liquid phase, which is a measure of the amount of HCG in said sample solution.

55. A method for the immunochemical determination of human chorionic gonadtropin (HCG), comprising:
(a) binding a known amount of HCG receptor protein to the surface of a water-insoluble, water-insuspensible solid carrier;
(b) contacting said bound receptor protein with a sample solution containing the unknown HCG to be determined;
(c) allowing sufficient time for an immunochemical reaction between the bound receptor protein and the HCG in the sample solution to take place, to bind the HCG to be determined to the insolubilized HCG receptor protein, forming a first solid phase and leaving a first liquid phase;

(d) separating the first solid phase from the first liquid phase;

(e) contacting said first solid phase and insolubilized HCG therein with a known amount of a reagent consisting essentially of dispersion particles of a hydrophobic dye or pigment having a particle size of at least 5 nm and having rabbit anti-HCG immunoglobulin attached to their surfaces;

(f) allowing sufficient time for a second immunological reaction to occur to bind said reagent to that part of said insolubilized HCG which has undergone the reaction in step (c), to form a second solid phase and a second liquid phase;

(g) separating the second solid phase from the second liquid phase; and (h) determining the amount of dye or pigment in the second solid phase or the second liquid phase, which is a measure of the HCG to be determined in said sample solution.

56. A test kit, to be used for the determination of a first component of an immunochemical reaction in an aqueous medium, selected from the group consisting of a specific binding protein and the corresponding bindable substance, according to a predetermined protocol, comprising:
   (a) a reagent consisting essentially of dispersion particles of a hydrophobic dye or pigment having a particle size of at least 5 nm and having attached to their surfaces either a component immunochemically similar to said first component to be determined, or a binding partner of the first component; and
   (b) directions for the performance of said protocol.

57. A test kit, to be used for the determination of a first component of an immunochemical reaction in an aqueous medium, selected from the group consisting of a specific binding protein and the corresponding bindable substance, according to a predetermined protocol, comprising:
   (a) a reagent consisting essentially of dispersion particles of a hydrophobic dye or pigment having a particle size of at least 5 nm and having attached to their surfaces (1) either a component immunochemically similar to said first component, or a binding partner to said first component, and (2) an immunochemically inert macromolecule; and
   (b) directions for the performance of said protocol.

58. A test kit, to be used for the determination of a first component of an immunochemical reaction in an aqueous medium, selected from the group consisting of a specific binding protein and the corresonding bindable substance, according to a predetermined protocol, comprising:
   (a) a reagent consisting essentially of dispersion particles of a hydrophobic dye or pigment having a particle size of at least 5 nm and having attached to their surfaces a coating of an inert hydrophilic polymer or copolymer, the surface of each coated particle having attached to it a component selected from the group consisting of a component immunochemically equivalent to said first component, or a binding partner to said first component; and
   (b) directions for the performance of said protocol.

59. A freeze-dried reagent for use in an immunoassay, consisting essentially of dispersion particles of a hydrophobic dye or pigment having attached to their surfaces an immunochemical component, said particle having a particles size of at least 5 nm.

60. The reagent of claim 59 wherein said dye is Palanil Red BF and said immunochemical component is rabbit anti-HCG immunoglobulin.

61. A freeze-dried reagent for use in an immunoassay to determine a first immunochemical component, consisting essentially of dispersion particles of a hydrophobic dye or pigment having a particles size of at least 5 nm and having attached to their surfaces (i) a component immunochemically equivalent to the first component to be determined and (ii) an immunochemically inert macromolecule.

62. A freeze-dried reagent for use in an immunoassay to determine a first immunochemical component, consisting essentially of dispersion particles of a hydrophobic dye or pigment having a coating of an inert hydrophilic polymer or copolymer, the surface of each coated particle having attached to it a component which is immunochemically similar to said first component, and said particles having a particle size of at least 5 nm.

63. A test kit, to be used for the detection and/or determination of at least one component of the reaction between a specific binding protein and a corresponding bindable substance thereto in an aqueous medium according to a predetermined protocol, comprising:
   (a) a known amount of a dye- or pigment-labelled component obtained by coupling a component of said reaction to particles of (1) a hydrophobic dye or pigment or (2) polymer nuclei coated with a hydrophobic dye or pigment, said particles having a particle size of at least 5 nm;
   (b) a known amount of at least one additional immunochemical reagent, at least one of said reagents being a ligand or an immobilized ligand, which ligand is selected from the group consisting of
      (aa) a ligand capable of binding with the dye- or pigment-labelled component (a);
      (bb) a ligand capable of binding with a binding partner of the dye- or pigment-labelled component (a);
      (cc) a ligand capable binding with at least one of the component(s) to be determined; and
      (dd) a ligand capable of binding with at least one of the binding partners of at least one of the component(s) to be determined; and
   (c) directions for the performance of a protocol for the detection and/or determination of at least one component of an immunochemical reaction in an aqueous medium between a specific binding protein and a corresponding bindable substance thereto.

64. A reagent for use in an immunoassay to determine a first immunochemical component, consisting essentially of dispersion particles of a hydrophobic dye or a pigment having attached to their surfaces (1) either a component immunochemically similar to said first component, or a binding partner to said first component, and (2) an immunochemically inert macromolecule, said particles having a particle size of at least 5 nm.

65. The reagent of claim 64 wherein said dye is Palanil Red BF, the component (1) is rabbit (anti HCG) immunoglobulin, and said immunochemically inert macromolecule is bovine serum albumin.

* * * * *

UNITED STATES PATENT AND TRADEMARK OFFICE
CERTIFICATE OF CORRECTION

PATENT NO. : 4,373,932
DATED : Feb. 15, 1983
INVENTOR(S) : Gribnau et al.

It is certified that error appears in the above—identified patent and that said Letters Patent is hereby corrected as shown below:

Title page, first column, 8 entries from the end, "Leburdy" should read -- Liburdy --.

under "OTHER PUBLICATIONS", there should be added:

-- F. Kohen, et al., "Non-Radioisotopic Homogeneous Steroid Immunoassays", Journal of Steroid Biochemistry, 11, pp. 161-167 (1979).

T. C. Gribnau, et al., "Immunosorbents Based on Halopyrimidines or Reactive Azodye Activated Polysaccharide Matrices", Protides Biol. Fluids, 27, pp. 793-796 (1980).

R. F. Schall, Jr., et al., "Alternatives to Radioimmunoassay: Labels and Methods," Clinical Chemistry, 27 (7), pp. 1157-1164. --

UNITED STATES PATENT AND TRADEMARK OFFICE
CERTIFICATE OF CORRECTION

PATENT NO. : 4,373,932
DATED : Feb. 15, 1983
INVENTOR(S) : Gribnau et al.

It is certified that error appears in the above—identified patent and that said Letters Patent is hereby corrected as shown below:

Column 3, line 29, "color" should be -- Color --.

Column 7, line 41, "above" should be -- above) --.

Column 9, line 43, "$^\mu$max" should be -- $^\lambda$max";

line 54, "blanc" should be -- blank --.

Column 13, line 17, "derivate" should be -- derivative --;

line 36 should read -- tion). --.

Column 14, line 11, "choosen" should read -- chosen --;

line 19, "volume" should read -- volumes --.

Column 18, line 56, "(HCG-HRP) should read -- (HCG-HRP)* --.

Column 19, line 3, "(HCG-HRP)" should read -- (HCG-HRP)* --.

Column 30, line 62, "containing" should read -- contacting --;

line 67, "of" (second occurence) should read -- or --

Column 34, line 65, "separting" should read -- separating --.

Column 35, line 17, -- liquid -- should be inserted after "first".

UNITED STATES PATENT AND TRADEMARK OFFICE
CERTIFICATE OF CORRECTION

PATENT NO. : 4,373,932

DATED : Feb. 15, 1983

INVENTOR(S) : Gribnau et al.

It is certified that error appears in the above—identified patent and that said Letters Patent is hereby corrected as shown below:

Column 37, line 36, "testosterone" should be -- HPL --.

Column 38, line 35 "globuliln" should read -- globulin --;

line 60, "44" should be -- 49 --.

Column 39, line 40, "or" should be -- of --.

Column 41, line 51, "corresonding" should be

-- corresponding --.

Signed and Sealed this

Nineteenth Day of July 1983

[SEAL]

Attest:

GERALD J. MOSSINGHOFF

Attesting Officer

Commissioner of Patents and Trademarks